US010813853B2

(12) United States Patent
Tan et al.

(10) Patent No.: US 10,813,853 B2
(45) Date of Patent: Oct. 27, 2020

(54) COMPOSITIONS AND METHODS FOR HAIR

(71) Applicant: L'OREAL, Paris (FR)

(72) Inventors: Siliu Tan, Westfield, NJ (US);
Jean-Thierry Simonnet, Rueil
Malmaison (FR); Jim Mitchell Singer,
South Orange, NJ (US); Nghi Van
Nguyen, Edison, NJ (US); Aditi
Gogineni, Rahway, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/586,105

(22) Filed: Dec. 30, 2014

(65) Prior Publication Data
US 2016/0184195 A1 Jun. 30, 2016

(51) Int. Cl.
A61Q 5/06 (2006.01)
A61K 8/06 (2006.01)
A61K 8/894 (2006.01)
A61K 8/81 (2006.01)
A61K 8/87 (2006.01)

(52) U.S. Cl.
CPC ............ A61K 8/062 (2013.01); A61K 8/8152 (2013.01); A61K 8/87 (2013.01); A61K 8/894 (2013.01); A61Q 5/06 (2013.01)

(58) Field of Classification Search
None
See application file for complete search history.

(56) References Cited

U.S. PATENT DOCUMENTS

| 3,110,695 | A | 11/1963 | Ceresa |
| 3,304,273 | A | 2/1967 | Stamberger |
| 3,383,351 | A | 5/1968 | Stamberger |
| 3,412,054 | A | 11/1968 | Milligan et al. |
| 3,523,095 | A | 8/1970 | Laurito et al. |
| 3,915,921 | A | 10/1975 | Schlatzer, Jr. |
| 4,003,699 | A | 1/1977 | Rose et al. |
| RE30,199 | E | 1/1980 | Rose et al. |
| 4,509,949 | A | 4/1985 | Huang et al. |
| 4,644,030 | A | 2/1987 | Loewrigkeit et al. |
| 4,710,374 | A | 12/1987 | Grollier et al. |
| 4,798,721 | A * | 1/1989 | Yahagi ............... A61K 8/02 424/70.11 |
| 4,985,239 | A | 1/1991 | Yahagi et al. |
| 5,061,289 | A | 10/1991 | Clausen et al. |
| 5,085,859 | A | 2/1992 | Halloran et al. |
| 5,156,911 | A | 10/1992 | Stewart |
| 5,173,526 | A | 12/1992 | Vijayendran et al. |
| 5,221,534 | A | 6/1993 | Deslauriers et al. |
| 5,380,340 | A | 1/1995 | Neunhoeffer et al. |
| 5,441,728 | A | 8/1995 | Tsaur et al. |
| 5,534,267 | A | 7/1996 | Neunhoeffer et al. |
| 5,565,216 | A | 10/1996 | Cowsar et al. |
| 5,618,523 | A | 4/1997 | Zysman et al. |
| 5,637,291 | A | 6/1997 | Bara et al. |
| 5,663,366 | A | 9/1997 | Neunhoeffer et al. |
| 5,679,327 | A | 10/1997 | Darkwa et al. |
| 5,708,151 | A | 1/1998 | Moeckli |
| 5,753,215 | A | 5/1998 | Mougin et al. |
| 5,766,576 | A | 6/1998 | Loewe et al. |
| 5,932,194 | A | 8/1999 | Plessix et al. |
| 6,013,682 | A | 1/2000 | Dalle et al. |
| 6,099,592 | A | 8/2000 | Vidal et al. |
| 6,110,451 | A | 8/2000 | Matz et al. |
| 6,120,778 | A | 9/2000 | Simonnet |
| 6,126,929 | A | 10/2000 | Mougin |
| 6,126,948 | A | 10/2000 | Simonnet et al. |
| 6,165,446 | A | 12/2000 | Samain et al. |
| 6,214,328 | B1 * | 4/2001 | Chang et al. ............... 424/70.16 |
| 6,268,431 | B1 * | 7/2001 | Snyder ................... A61K 8/068 424/70.11 |
| 6,284,003 | B1 | 9/2001 | Rose et al. |
| 6,338,741 | B1 | 1/2002 | Vidal et al. |
| 6,399,050 | B1 | 6/2002 | Pasquet et al. |
| 6,464,990 | B2 | 10/2002 | Simonnet et al. |
| 6,482,394 | B1 | 11/2002 | Schehlmann et al. |
| 6,585,965 | B1 | 7/2003 | Carballada et al. |

(Continued)

FOREIGN PATENT DOCUMENTS

| DE | 1152536 B | 8/1963 |
| DE | 2359399 A1 | 6/1975 |

(Continued)

OTHER PUBLICATIONS

Co-pending U.S. Appl. No. 14/576,639, Siliu Tan et al., "Hair Styling Compositions Comprising Latex Polymers," filed Dec. 19, 2014.
Co-pending U.S. Appl. No. 14/577,579, Siliu Tan et al., "Hair Styling Compositions Comprising Latex Polymers and Wax Dispersions," filed Dec. 19, 2014.
Co-pending U.S. Appl. No. 14/577,740, Christine Shin et al., "Hair Cosmetic Composition Containing Latex Polymers and a Silicone-Organic Polymer Compound," filed Dec. 19, 2014.
Co-pending U.S. Appl. No. 14/577,809, Mark Benn, "Hair Coloring Compositions Comprising Latex Polymers," filed Dec. 19, 2014.
Co-pending U.S. Appl. No. 14/578,074, Siliu Tan et al., "Compositions and Methods for Hair," filed Dec. 19, 2014.
Co-pending U.S. Appl. No. 14/578,122, Christine Shin, "Hair Cosmetic Composition Containing a Polyurethane Latex Polymer and a Silicone Organic Polymer Compound," filed Dec. 19, 2014.

(Continued)

Primary Examiner — Jyothsna A Venkat
(74) Attorney, Agent, or Firm — The Marbury Law Group, PLLC

(57) ABSTRACT

Disclosed are oil-in-water (O/W) emulsions comprising (a) an aqueous dispersion of particles of at least one latex chosen from an acrylate latex, a polyurethane latex, or a silicone latex, (b) an oil phase, and (c) at least one surfactant, wherein the amount of the (a) aqueous dispersion of particles of at least one latex chosen from an acrylate latex, a polyurethane latex, or a silicone latex, in combination with the (c) at least one surfactant is sufficient to stabilize the oil-in-water emulsion. The disclosure also relates to hair styling and/or shaping compositions comprising the O/W emulsions, methods of making the emulsions, and methods of styling and/or shaping the hair.

17 Claims, No Drawings

(56) References Cited

U.S. PATENT DOCUMENTS

| | | |
|---|---|---|
| 6,592,633 B2 | 7/2003 | Lang et al. |
| 6,613,315 B1 | 9/2003 | Dupuis |
| 6,645,258 B2 | 11/2003 | Vidal et al. |
| 6,703,028 B1 | 3/2004 | Samain et al. |
| 6,726,916 B1 | 4/2004 | Ramin |
| 6,730,789 B1 | 5/2004 | Birault et al. |
| 6,946,123 B2 | 9/2005 | De La Poterie et al. |
| 7,211,244 B2 | 5/2007 | Auguste et al. |
| 7,651,693 B2 | 1/2010 | Merlau et al. |
| 7,740,832 B1 | 6/2010 | Rollat-Corvol et al. |
| 7,785,613 B2 | 8/2010 | Collin et al. |
| 7,842,286 B2 * | 11/2010 | Walter .................. A61K 8/86 424/70.122 |
| 7,993,632 B2 | 8/2011 | Lezer et al. |
| 8,343,238 B1 | 1/2013 | Lopez et al. |
| 8,398,961 B2 | 3/2013 | Kaplan et al. |
| 8,691,200 B2 | 4/2014 | Vilbert |
| 8,865,147 B2 | 10/2014 | Rizk et al. |
| 2002/0007521 A1 | 1/2002 | Lang et al. |
| 2002/0010970 A1 | 1/2002 | Cottard et al. |
| 2002/0022009 A1 | 2/2002 | De La Poterie et al. |
| 2002/0050013 A1 | 5/2002 | Vidal et al. |
| 2002/0055562 A1 | 5/2002 | Butuc |
| 2002/0198328 A1 | 12/2002 | L'Alloret |
| 2003/0019051 A9 | 1/2003 | Vidal et al. |
| 2003/0026815 A1 | 2/2003 | Scott et al. |
| 2003/0044440 A1 | 3/2003 | Toumi |
| 2003/0053976 A1 | 3/2003 | Tournilhac et al. |
| 2003/0059377 A1 | 3/2003 | Riley |
| 2003/0059388 A1 * | 3/2003 | Auguste ............... A61K 8/044 424/70.1 |
| 2003/0064045 A1 | 4/2003 | Tournilhac et al. |
| 2003/0103927 A1 | 6/2003 | Maubru |
| 2003/0138465 A9 | 7/2003 | Douin et al. |
| 2003/0147832 A1 | 8/2003 | L'Alloret |
| 2003/0161804 A1 | 8/2003 | Perron et al. |
| 2004/0071646 A1 | 4/2004 | Pataut et al. |
| 2004/0096474 A1 | 5/2004 | Merlau et al. |
| 2004/0214913 A1 | 10/2004 | L'Alloret |
| 2005/0008605 A1 | 1/2005 | L'Alloret |
| 2005/0020779 A1 | 1/2005 | Mougin et al. |
| 2005/0025736 A1 | 2/2005 | Jachowicz et al. |
| 2005/0048016 A1 | 3/2005 | Lebreton et al. |
| 2005/0053568 A1 | 3/2005 | Aubrun-Sonneville et al. |
| 2005/0065253 A1 | 3/2005 | Collin et al. |
| 2005/0089490 A1 | 4/2005 | Jachowicz et al. |
| 2006/0115446 A1 | 6/2006 | Rollat-Corvol et al. |
| 2006/0134043 A1 | 6/2006 | Nakamura |
| 2006/0182702 A1 | 8/2006 | Lazzeri et al. |
| 2006/0292095 A1 | 12/2006 | Biatry et al. |
| 2007/0031361 A1 | 2/2007 | Herrmann et al. |
| 2007/0190008 A1 | 8/2007 | Campain et al. |
| 2007/0224140 A1 | 9/2007 | Quadir et al. |
| 2007/0286833 A1 | 12/2007 | Keller et al. |
| 2008/0138307 A1 | 6/2008 | Bazemore et al. |
| 2008/0175808 A1 | 7/2008 | Pavel |
| 2008/0305064 A1 | 12/2008 | Bui et al. |
| 2009/0035335 A1 | 2/2009 | Marotta et al. |
| 2009/0060858 A1 | 3/2009 | Schwarzwaelder et al. |
| 2009/0074695 A1 | 3/2009 | Mahe et al. |
| 2009/0280076 A1 | 11/2009 | Yoshida et al. |
| 2009/0297467 A1 | 12/2009 | Laurent et al. |
| 2009/0317432 A1 | 12/2009 | Kergosien |
| 2010/0028284 A1 | 2/2010 | Atis et al. |
| 2010/0119467 A1 * | 5/2010 | Dumousseaux ......... A61K 8/06 424/70.7 |
| 2010/0189678 A1 | 7/2010 | Knappe et al. |
| 2010/0278770 A1 | 11/2010 | Arditty et al. |
| 2011/0014139 A1 | 1/2011 | Viala et al. |
| 2011/0015279 A1 | 1/2011 | Doerr et al. |
| 2011/0097289 A1 | 4/2011 | Viala et al. |
| 2011/0097293 A1 | 4/2011 | Grey et al. |
| 2011/0150802 A1 | 6/2011 | Bui et al. |
| 2011/0150807 A1 * | 6/2011 | Bui ...................... A61K 8/044 424/70.7 |
| 2012/0247500 A1 | 10/2012 | Plos et al. |
| 2012/0282309 A1 | 11/2012 | Dihora et al. |
| 2012/0308496 A1 | 12/2012 | Viala et al. |
| 2013/0084256 A1 | 4/2013 | Li et al. |
| 2013/0167863 A1 | 7/2013 | Schmelz et al. |
| 2013/0171084 A1 | 7/2013 | Kawaratani et al. |
| 2013/0284198 A1 | 10/2013 | Rizk et al. |
| 2014/0102468 A1 | 4/2014 | Pistorio et al. |
| 2014/0105845 A1 | 4/2014 | Bui et al. |
| 2014/0105945 A1 | 4/2014 | Bui et al. |
| 2014/0186270 A1 | 7/2014 | Suleiman et al. |
| 2015/0004119 A1 | 1/2015 | Tan et al. |

FOREIGN PATENT DOCUMENTS

| | | |
|---|---|---|
| DE | 2364398 A1 | 10/1975 |
| DE | 3843892 A1 | 6/1990 |
| DE | 4133957 A1 | 4/1993 |
| DE | 19543988 A1 | 5/1997 |
| DE | 102009054516 A1 | 6/2011 |
| EP | 0216479 A1 | 4/1987 |
| EP | 0692237 A1 | 1/1996 |
| EP | 0714954 A2 | 6/1996 |
| EP | 0770375 A1 | 5/1997 |
| EP | 0847752 A1 | 6/1998 |
| EP | 0874017 A2 | 10/1998 |
| EP | 0898958 A1 | 3/1999 |
| EP | 0898960 A1 | 3/1999 |
| EP | 1082953 A1 | 3/2001 |
| EP | 1291051 A2 | 3/2003 |
| EP | 1466588 A1 | 10/2004 |
| EP | 1652509 A2 | 5/2006 |
| EP | 2356981 A1 | 8/2011 |
| EP | 2570192 A1 | 3/2013 |
| FR | 2633940 B3 | 7/1991 |
| FR | 2733749 A1 | 11/1996 |
| FR | 2774899 A1 | 8/1999 |
| FR | 2801308 A1 | 5/2001 |
| FR | 2834458 A1 | 7/2003 |
| FR | 2856923 A1 | 1/2005 |
| FR | 2889943 A1 | 3/2007 |
| FR | 2898050 A1 | 9/2007 |
| FR | 2961103 A1 | 12/2011 |
| FR | 2968978 A1 | 6/2012 |
| GB | 1026978 A | 4/1966 |
| GB | 1040452 A | 8/1966 |
| GB | 1153196 A | 5/1969 |
| JP | H021956 A | 1/1990 |
| JP | H05163124 A | 6/1993 |
| KR | 20100105168 A | 9/2010 |
| WO | 9408969 A1 | 4/1994 |
| WO | 9408970 A1 | 4/1994 |
| WO | 9501772 A1 | 1/1995 |
| WO | 9515144 A1 | 6/1995 |
| WO | 9615765 A1 | 5/1996 |
| WO | 0119333 A1 | 3/2001 |
| WO | 2005100444 A1 | 10/2005 |
| WO | 2007/102972 A1 | 9/2007 |
| WO | 2007099269 A2 | 9/2007 |
| WO | 2010133658 A2 | 11/2010 |
| WO | 2011056332 A1 | 5/2011 |
| WO | 2011069786 A2 | 6/2011 |
| WO | 2011137338 A2 | 11/2011 |
| WO | 2012049146 A1 | 4/2012 |
| WO | 2012/072774 A1 | 6/2012 |
| WO | 2013059106 A1 | 4/2013 |
| WO | 2013074210 A1 | 5/2013 |
| WO | 2013092378 A1 | 6/2013 |
| WO | 2013092379 A1 | 6/2013 |
| WO | 2013092380 A1 | 6/2013 |
| WO | 2013092381 A1 | 6/2013 |
| WO | 2013092382 A1 | 6/2013 |
| WO | 2013092562 A1 | 6/2013 |
| WO | 2013092779 A2 | 6/2013 |
| WO | 2013092788 A1 | 6/2013 |
| WO | 2014001390 A1 | 1/2014 |
| WO | 2014001391 A1 | 1/2014 |
| WO | 2014/058856 A1 | 4/2014 |

(56) References Cited

FOREIGN PATENT DOCUMENTS

| WO | 2014/062334 A1 | 4/2014 |
|---|---|---|
| WO | 2014071354 A1 | 5/2014 |
| WO | 2014124066 A1 | 8/2014 |

OTHER PUBLICATIONS

Co-pending U.S. Appl. No. 13/931,329; Siliu Tan et al., "Compositions and Methods for Treating Hair," filed Jun. 28, 2013.
Co-pending U.S. Appl. No. 13/931,187; Siliu Tan et al., "Compositions and Methods for Treating Hair," filed Jun. 28, 2013.
Co-pending U.S. Appl. No. 13/931,204; Siliu Tan et al., "Compositions and Methods for Treating Hair," filed Jun. 28, 2013.
Co-pending U.S. Appl. No. 13/931,222; Siliu Tan et al., "Compositions and Methods for Treating Hair," filed Jun. 28, 2013.
Co-pending U.S. Appl. No. 13/931,238; Siliu Tan et al., "Compositions and Methods for Treating Hair," filed Jun. 28, 2013.
Co-pending U.S. Appl. No. 13/931,248; Siliu Tan et al., "Compositions and Methods for Treating Hair," filed Jun. 28, 2013.
Co-pending U.S. Appl. No. 13/931,260; Siliu Tan et al., "Compositions and Methods for Treating Hair," filed Jun. 28, 2013.
Co-pending U.S. Appl. No. 13/931,276; Siliu Tan et al., "Compositions and Methods for Treating Hair," filed Jun. 28, 2013.
Co-pending U.S. Appl. No. 13/931,288; Siliu Tan et al., "Compositions and Methods for Treating Hair," filed Jun. 28, 2013.
Co-pending U.S. Appl. No. 13/931,298; Siliu Tan et al., "Compositions and Methods for Treating Hair," filed Jun. 28, 2013.
Co-pending U.S. Appl. No. 13/931,312; Siliu Tan et al., "Compositions and Methods for Treating Hair," filed Jun. 28, 2013.
English language abstract for EP 0770375 (May 2, 1997).
English language abstract for EP0898960 (Mar. 3, 1999).
English language abstract for EP1082953 (Mar. 14, 2001).
English language abstract for FR2633940 (Jul. 12, 1991).
English language abstract for FR2898050 (Sep. 7, 2007).
English language abstract for FR2968978 (Jun. 22, 2012).
English language Abstract of FR2834458 (Jul. 11, 2003).
Galgoci, Ernest C., et al., "Solvent-Free Urethane-Acrylic Hybrid Polymers for Coatings," JCT Coatings Tech, 2 (13), Feb. 2005, pp. 28-36.
International Search Report for Application No. PCT/US2014/044036, dated Oct. 21, 2014, 3 pages.
International Search Report for Application No. PCT/US2014/044377, dated Oct. 31, 2014, 3 pages.
International Search Report for Application No. PCT/US2014/044557, dated Oct. 13, 2014, 3 pages.
International Search Report for Application No. PCT/US2014/044587, dated Oct. 31, 2014, 3 pages.
International Search Report for Application No. PCT/US2014/044610, dated Oct. 31, 2014, 4 pages.
Jachowicz, J., et al., "Mechanical Analysis of Elasticity and Flexibility of Virgin and Polymer-Treated Hair Fiber Assemblies," J. Cosmet. Sci., 53, Nov./Dec. 2002, pp. 345-361.
Non-Final Office Action for U.S. Appl. No. 13/931,187, dated Feb. 13, 2015.
Non-Final Office Action for U.S. Appl. No. 13/931,204, dated Feb. 20, 2015.
Non-Final Office Action for U.S. Appl. No. 13/931,238, dated Feb. 13, 2015.
Non-Final Office Action for U.S. Appl. No. 13/931,248, dated Feb. 20, 2015.
Non-Final Office Action for U.S. Appl. No. 13/931,260, dated Feb. 20, 2015.
Non-Final Office Action for U.S. Appl. No. 13/931,276, dated Feb. 17, 2015.
Non-Final Office Action for U.S. Appl. No. 13/931,288, dated Feb. 18, 2015.
Non-Final Office Action for U.S. Appl. No. 13/931,298, dated Feb. 20, 2015.
Non-Final Office Action for U.S. Appl. No. 13/931,312, dated Feb. 18, 2015.
Non-Final Office Action for U.S. Appl. No. 13/931,329, dated Feb. 13, 2015.
Polyquats As Conditioning Agents, 2009. Retrieved from the Internet.
English language abstract for DE 102009054516 (Jun. 16, 2011).
English language abstract for EP 0847752 (Jun. 17, 1998).
English language abstract for FR 2961103 (Dec. 16, 2011).
English language abstract for JP H05-163124 (Jun. 29, 1993).
English language abstract for KR 20100105168 (Sep. 29, 2010).
Final Office Action for co-pending U.S. Appl. No. 13/931,187 (dated Jul. 20, 2015).
Non-Final Office Action for co-pending U.S. Appl. No. 13/931,222 (dated Apr. 7, 2015).
Non-Final Office Action for co-pending U.S. Appl. No. 14/577,809 (dated Jul. 10, 2015).
English language abstract for JP H021956 (Jan. 8, 1990).
Final Office Action for co-pending U.S. Appl. No. 13/931,222 (dated Jul. 28, 2015).
International Search Report and Written Opinion for copending Application No. PCT/US2015/066818, dated Feb. 26, 2016.
International Search Report and Written Opinion for counterpart Application PCT/US2015/065967, dated Jul. 5, 2016.
International Search Report and Written Opinion for counterpart Application PCT/US2015/065975, dated Jul. 5, 2016.
Extended European Search Report for counterpart EP Application No. 14817057.4, dated Nov. 2, 2016.
Extended European Search Report for counterpart EP Application No. 14818467.4, dated Nov. 9, 2016.
Extended European Search Report for counterpart EP Application No. 14818460.9, dated Nov. 21, 2016.
Extended European Search Report for counterpart EP Application No. 14817786.8, dated Oct. 14, 2016.

\* cited by examiner

COMPOSITIONS AND METHODS FOR HAIR

TECHNICAL FIELD

The disclosure relates to oil-in-water (O/W) emulsions comprising (a) an aqueous dispersion of particles of at least one latex chosen from an acrylate latex, a polyurethane latex, or a silicone latex, (b) an oil phase, and (c) at least one surfactant. The disclosure also relates to hair styling compositions comprising the O/W emulsions, methods of making the emulsions, and methods of styling the hair.

BACKGROUND

Compositions for styling the hair are known, such as, for example, hair spray compositions, hair gels and mousses, hair volumizing compositions, hair smoothing creams, lotions, serums, oils, clays, etc. The goals of many hair styling compositions include to hold or fix the hair in a particular shape, to impart or increase volume of the hair, and/or to smooth the hair, e.g. to decrease or eliminate the appearance of frizz.

Latexes are known for use in hair styling processes. However, the application to hair of these latexes may cause the hair to feel dry and sticky. Moreover, attempts to use latex film-formers along with oily protecting agents such as UV agents and/or antioxidants, which may be desired to protect the hair against UV and other environmental damage, have led to unsatisfactory results.

Hair styling compositions comprising water-insoluble substances, such as oils, UV agents, and/or antioxidants, are typically prepared as oil-in-water (O/W) emulsions, comprising an oily phase dispersed in an aqueous phase. However, conventional O/W emulsion products for the hair can also have drawbacks, such as an oily feel and lack of stability. In order to avoid some of these drawbacks, additional components such as surfactants may be added to stabilize the emulsion by creating a gelled matrix which serves to set, within its three-dimensional network, the globules of the oil phase, thereby mechanically maintaining the emulsion.

Traditionally, however, the presence of components such as surfactants and thickeners have limited the options for preparing O/W emulsions. For example, thickeners may limit the galenic form of the composition, and surfactants may limit the way in which the composition is prepared, i.e. it must be prepared with heating, thereby precluding heat-sensitive components that cannot withstand heating during the processing.

However, it has now been discovered that a stable O/W emulsion can be prepared by providing latex film forming polymer particles at the interface of the water phase and the oil phase, without forming a continuous closed capsule around the oily particle or droplet.

According to various embodiments, O/W emulsions comprising (a) an aqueous dispersion of particles of at least one latex chosen from an acrylate latex, a polyurethane latex, or a silicone latex, (b) an oil phase, and (c) at least one surfactant, are provided. Hair styling and/or shaping compositions comprising the O/W emulsions, methods of making the emulsions, and methods of styling and/or shaping the hair with the O/W emulsion or a composition comprising the O/W emulsion are also provided.

DESCRIPTION OF EXEMPLARY EMBODIMENTS

The disclosure relates, in various embodiments, to O/W emulsions comprising (a) an aqueous dispersion of particles of at least one latex chosen from an acrylate latex, a polyurethane latex, or a silicone latex, (b) an oil phase, and (c) at least one surfactant. According to at least various exemplary embodiments, the O/W emulsion is stable.

In further embodiments, hair styling and/or shaping compositions comprising the O/W emulsions, as well as methods of making the O/W emulsions, and methods of styling and/or shaping the hair using the O/W emulsion or the compositions, are disclosed.

Aqueous Phase

According to various exemplary embodiments of the disclosure, the aqueous phase of the O/W emulsion comprises an aqueous dispersion of particles of at least one latex chosen from an acrylate latex, a polyurethane latex, or a silicone latex.

As non-limiting examples of the aqueous dispersion of latex polymers that may be used, mention may be made, independently, of an aqueous dispersion of at least one acrylate latex polymer, an aqueous dispersion of at least one polyurethane latex polymer, and/or an aqueous dispersion of at least one silicone latex polymer. It should be noted, however, that aqueous dispersions of any combination of acrylate latex polymer particles, polyurethane latex polymer particles, and silicone latex polymer particles are intended to fall within the scope of the disclosure.

In at least certain embodiments of the disclosure, the aqueous dispersion of particles of at least one latex may be obtained through an emulsion polymerization of monomers, for example where the resulting latex polymers have a particle size up to about 1 µm. For example, the particle size of the latex may range from about 50 nm to about 800 nm, or from about 100 nm to about 500 nm. Such particle sizes may, for example, be measured by a laser granulometer, (e.g. Brookhaven BI90).

In at least one exemplary embodiment, a dispersion prepared by the polymerization in water of one or more monomers having a polymerizable double bond may be chosen. In further exemplary embodiments, particles of acrylate and/or polyurethane and/or silicone particles may be prepared by known methods, e.g. by spray-drying or by condensation reactions between monomers, and the particles subsequently dispersed in an aqueous medium.

The dispersion medium comprises at least one solvent chosen from water. The dispersion medium may further comprise at least one solvent chosen from cosmetically acceptable organic solvents. Cosmetically acceptable organic solvents may, in various embodiments, be water-miscible, e.g. capable of forming at 25° C. a homogeneous mixture that is transparent, or substantially transparent, to the eye. For instance, cosmetically acceptable organic solvents may be chosen from lower monoalcohols, such as those containing from about 1 to 5 carbon atoms, for example ethanol and isopropanol; polyols, including glycols, such as those containing from about 2 to 8 carbon atoms, for example propylene glycol, ethylene glycol, 1,3-butylene glycol, dipropylene glycol, hexylene glycol, and glycerin; hydrocarbons, such as, for example, isododecane and mineral oil; and silicones, such as dimethicones, cyclomethicones, and cyclopentasiloxane; as well as mixtures thereof. For example, the at least one cosmetically acceptable organic solvent of the dispersion medium may, in at least certain exemplary embodiments, comprise greater than 50%, such as greater than 55%, greater than 60%, greater than 65%, greater than 70%, greater than 75%, greater than 80%, greater than 85%, greater than 90%, greater than 95%, greater than 96%, greater than 97%, greater than 98%, or greater than 99% by weight, relative to the total weight of the dispersion medium.

In at least one embodiment, the solvent of the dispersion medium consists of water. In other embodiments, the solvent of the dispersion medium consists of water and at least one cosmetically acceptable organic solvent. In further embodiments, the solvent comprises water. In yet further embodiments, the solvent of the dispersion medium primarily comprises water. For example, the solvent of the dispersion medium may, in at least certain exemplary embodiments, comprise greater than 50% water, such as greater than 55% water, greater than 60% water, greater than 65% water, greater than 70% water, greater than 75% water, greater than 80% water, greater than 85% water, greater than 90% water, greater than 95% water, greater than 96% water, greater than 97% water, greater than 98% water, or greater than 99% water.

In embodiments according to the disclosure, the particles of the at least one latex are not soluble in the solvent of the dispersion medium, i.e. are not water soluble and/or are not soluble in the at least one cosmetically acceptable organic solvent. Accordingly, the latex polymers retain their particulate form in the solvent or solvents chosen.

In various embodiments, the aqueous phase of the O/W dispersion may comprise the at least one latex in an amount up to about 10%, such as up to about 8%, up to about 6%, up to about 4%, up to about 2%, or up to about 1% by weight as polymeric active material (dry weight basis), relative to the total weight of the emulsion. For example, the aqueous phase may comprise an amount of the at least one latex ranging from about 0.1% to about 10%, such as from about 0.5% to about 9%, from about 1% to about 8%, from about 1.5% to about 7%, or from about 2% to about 6%, by weight as polymeric active material (dry weight basis), relative to the total weight of the emulsion, including all ranges and subranges there between.

In certain embodiments where more than one latex polymer is present in the aqueous phase of the O/W emulsion, the latex polymers may be present in the aqueous phase in a combined amount ranging up to about 10%, such as up to about 8%, up to about 6%, up to about 4%, up to about 2%, or up to about 1% by weight as polymeric active material (dry weight basis), relative to the total weight of the emulsion. For example, the aqueous phase may comprise from about 0.1% to about 10%, such as from about 0.5% to about 9%, from about 1% to about 8%, from about 1.5% to about 7%, or from about 2% to about 6%, by weight as polymeric active material (dry weight basis), relative to the total weight of the emulsion, including all ranges and subranges there between.

According to various exemplary embodiments where more than one latex polymer is chosen, e.g. in an embodiment where an acrylate latex and a polyurethane latex are chosen, where an acrylate latex and a silicone latex are chosen, where an acrylate latex, a polyurethane latex, and a silicone latex are chosen, where two acrylate latexes, two polyurethane latexes, and/or two silicone latexes are chosen, etc., the more than one latex polymers may optionally each be dispersed in independent dispersion media. In yet further embodiments, the more than one latex polymer may optionally be dispersed together in the same dispersion medium.

In at least certain exemplary embodiments, latex particles according to the disclosure may have an average diameter ranging up to about 1 μm, such as from about 50 nm to about 800 nm, or from about 100 nm to about 500 nm. Such particle sizes may be measured by any method known, such as with a laser granulometer (e.g. Brookhaven BI90).

In various embodiments, the particles of the acrylate latex, polyurethane latex, and/or silicone latex may, independently, be partially unneutralized, or unneutralized. In at least certain embodiments where the latex particles are unneutralized or partially unneutralized, the particle size may be, for example, greater than about 800 nm. In various embodiments, the particulate form of the latex polymers is retained in the dispersion medium.

In further embodiments, the particles of the acrylate latex, polyurethane latex, and/or silicone latex may be chosen from uncharged and charged latex polymers. Thus, the acrylate latex, polyurethane latex, and/or silicone latex polymers may, according to various exemplary embodiments, be chosen from nonionic latex polymers, cationic latex polymers, and anionic latex polymers.

According to various exemplary embodiments, the aqueous latex dispersions may optionally be stabilized by anionic, nonionic, cationic, and amphoteric surfactants, as well as mixtures thereof. In one embodiment, the latex dispersions may be stabilized by one or more anionic surfactants; in yet a further embodiment, the latex dispersions may be stabilized by one or more cationic surfactants; and in yet a further embodiment, the aqueous dispersion is not stabilized by a surfactant.

According to various exemplary and non-limiting embodiments, the acrylate and/or polyurethane latex polymers may be chosen from (A) acrylate and/or polyurethane latex polymers having a glass transition temperature (Tg) ranging from about −90° C. to about 40° C., a Young's modulus ranging from about 0.5 MPa to about 500 MPa, and a strain, under stress at 18 N, of at least about 1%; and/or (B) acrylate and/or polyurethane latex polymers having a glass transition temperature (Tg) ranging from about 40° C. to about 200° C., a Young's modulus ranging from about 500 MPa to about 5 GPa, and a strain, under stress at 18 N, of lower than about 2%. In at least one embodiment, the aqueous dispersions comprises at least one polymer (A) and at least one polymer (B).

The physical properties of the film or coating produced by the latex polymers (a) on a surface may be evaluated using Q800 Dynamic Mechanical Analysis from TA Instrument, and tested in a DMA Control Force mode. A stress/strain test is conducted by using a preload force of 0.001N, isothermal temperature at 25° C., soak time of 0.5 minutes, force ramp rate of 0.5N/min to 18 N. The test ends when the sample breaks, 18 N force is reached, or maximum displacement is achieved (25.5 mm). From the stress/strain curve, the Young's Modulus is calculated as the slope of the linear portion at about 0.01% Strain to about 1% Strain. From the stress/strain curve, the % Strain at the stress of 0.5 MPa can be reported. The latex film was obtained by allowing a 30 gram water solution containing 4 grams of the latex polymer(s) to dry slowly in a 100 mL PFA Petri dish (100 mm diameter×15 mm height) at room temperature for at least 3 days.

Acrylate Latex Polymers

In various exemplary and non-limiting embodiments, the acrylate latex polymers may be chosen from film-forming and non-film-forming acrylate latex polymers, such as those resulting from the homopolymerization or copolymerization of monomers chosen from (meth)acrylics, (meth)acrylates, (meth)acrylamides and/or vinyl homopolymers or copolymers. The term "(meth)acryl" and variations thereof, as used herein, means acryl or methacryl.

The (meth)acrylic monomers may be chosen from, for example, acrylic acid, methacrylic acid, citraconic acid, itaconic acid, maleic acid, fumaric acid, crotonic acid, and maleic anhydride. Additional non-limiting examples of (meth)acrylic monomers include C1-C8 alkyl (meth)acrylic, such as, for example, methyl (meth)acrylic, ethyl (meth)acrylic, propyl (meth)acrylic, isopropyl (meth)acrylic, butyl (meth)acrylic, tert-butyl (meth)acrylic, pentyl(meth) acrylic, isopentyl (meth)acrylic, neopentyl (meth)acrylic, hexyl (meth)acrylic, isohexyl (meth)acrylic, 2-ethylhexyl (meth)acrylic, cyclohexyl (meth)acrylic, isohexyl (meth)acrylic, heptyl (meth)acrylic, isoheptyl (meth)acrylic, octyl (meth)acrylic, isooctyl (meth)acrylic, as well as combinations of any of the above.

The esters of (meth)acrylic monomers may be, by way of non-limiting example, C1-C8 alkyl (meth)acrylates such as methyl (meth)acrylate, ethyl (meth)acrylate, propyl (meth)acrylate, isopropyl (meth)acrylate, butyl (meth)acrylate, tert-butyl (meth)acrylate, pentyl(meth) acrylate, isopentyl (meth)acrylate, neopentyl (meth)acrylate, hexyl (meth)acrylate, isohexyl (meth)acrylate, 2-ethylhexyl (meth)acrylate, cyclohexyl (meth)acrylate, isohexyl (meth)acrylate, heptyl (meth)acrylate, isoheptyl (meth)acrylate, octyl (meth)acrylate, isooctyl (meth)acrylate, allyl (meth)acrylate, and combinations thereof. Additional and non-limiting examples include C1-C8 alkoxy (meth)acrylates, such as methoxy (meth)acrylate, ethoxy (meth)acrylate, propyl oxide (meth) acrylate, isopropyl oxide (meth)acrylate, butyl oxide (meth) acrylate, tert-butyl oxide (meth)acrylate, pentyl oxide (meth) acrylate, isopentyl oxide (meth)acrylate, neopentyl oxide (meth)acrylate. The esters may be, by way of non-limiting example, C2-C6 hydroxy alkyl (meth)acrylates, such as hydroxy ethyl (meth)acrylate, 2-hydroxypropyl (meth)acrylate, glycidyl (meth)acrylate, ethylene glycol di(meth)acrylate, polyethylene glycol mono(meth)acrylate, 1,4-butane diol di(meth)acrylate, 1,6,hexane diol di(meth)acrylate, and any combination thereof. The esters may be, by way of non-limiting example, aryl (meth)acrylates such as benzyl (meth)acrylate, phenyl (meth)acrylate, and any combination thereof. The esters can further contain amino groups such as aminoethyl (meth)acrylate, N,N-dimethylaminoethyl (meth)acrylate, N,N-dimethylaminopropyl (meth)acrylate, N,N-dimethylaminodimethylpropyl (meth) acrylate, N,N-diethyleaminoethyl (meth)acrylate, and N,N, N-trimethylaminoethyl (meth)acrylate; and salts of the ethylenic amines.

According to at least certain exemplary embodiments, the alkyl group of the esters may be either fluorinated or perfluorinated, e.g. some or all of the hydrogen atoms of the alkyl group are substituted with fluorine atoms. The monomers can also be fluorine-containing monomers, such as, by way of non-limiting example, trifluoroethyl methacrylate, 2,2,3,3-tetrafluoropropyl methacrylate, 2,2,3,3,4,4-hexafluorobutyl methacrylate, perfluorooctyl methacrylate and perfluorooctyl acrylate; and silicone macromonomers.

The amides of (meth)acrylic monomers can, for example, be made of (meth)acrylamides, and especially N-alkyl (meth)acrylamides, in particular N-(C1-C12) alkyl (meth)acrylates such as N-ethyl (meth)acrylamide, N-t-butyl (meth)acrylamide, N-t-octyl (meth)acrylamide, N-methylol (meth)acrylamide and N-diacetone (meth)acrylamide, and any combination thereof.

The vinyl monomers can include, but are not limited to, vinyl cyanide compounds such as acrylonitrile and methacrylonitrile; vinyl esters such as vinyl formate, vinyl acetate, vinyl propionate, vinyl neodecanoate, vinyl pivalate, vinyl benzoate and vinyl t-butyl benzoate, triallyl cyanurate; vinyl halides such as vinyl chloride and vinylidene chloride; aromatic mono- or divinyl compounds such as styrene, α-methylstyrene, chlorostyrene, alkylstyrene, divinylbenzene and diallyl phthalate, and combination thereof. Other non-limiting ionic monomers can include para-styrensulfonic, vinylsulfonic, 2-(meth)acryloyloxyethylsulfonic, 2-(meth)acrylamido-2-methylpropylsulfonic acids.

The list of monomers given is not limiting, and it should be understood that it is possible to use any monomer known to those skilled in the art which includes acrylic and/or vinyl monomers (including monomers modified with a silicone chain).

Silicone acrylic polymers may also optionally be used as vinyl polymer in at least one exemplary and non-limiting embodiment.

In at least certain, non-limiting exemplary embodiments, acrylic latex polymers may be chosen from aqueous dispersions of Methacrylic Acid/Ethyl Acrylate copolymer (INCI: Acrylates Copolymer, such as LUVIFLEX® SOFT by BASF), PEG/PPG-23/6 Dimethicone Citraconate/C10-30 Alkyl PEG-25 Methacrylate/Acrylic Acid/Methacrylic Acid/Ethyl Acrylate/Trimethylolpropane PEG-15 Triacrylate copolymer (INCI: Polyacrylate-2 Crosspolymer, such as FIXATE SUPERHOLD™ by Lubrizol), Styrene/Acrylic copolymer (such as NEOCRYL® A-1120, DSM), Ethylhexyl Acrylate/Methyl Methacrylate/Butyl Acrylate/Acrylic Acid/Methacrylic Acid copolymer (INCI: Acrylates/Ethylhexyl Acrylate Copolymer, such as DAITOSOL 5000SJ, Daito Kasei Kogyo), Acrylic/Acrylates Copolymer (INCI name: Acrylates Copolymer, such as DAITOSOL 5000AD, Daito Kasei Kogyo), and Acrylic copolymers and Acrylates Copolymers, such as those known under the tradenames VINYSOL 2140 (Daido Chemical), ACULYN™ 33 (Dow Chemical), LUVIMER® MAE (BASF), or BALANCE CR (AKZO NOBEL), Styrene/Acrylates Copolymer, known under the tradename JONCRYL 77 from BASF, Styrene/Acrylates/Ammonium Methacrylate Copolymer, known under the tradename SYNTRAN PC5620 CG from Interpolymer, Styrene/Acrylates Copolymer sold under the tradename ACUDYNE BOLD (Dow Chemical), Acrylates/Hydroxyesters Acryaltes Copolymer sold under the tradename ACUDYNE DHR (Dow Chemical), Acrylates Copolymer sold under the tradename DERMACRYL C (Akzo Nobel), and mixtures thereof.

Polyurethane Latex Polymers

In various exemplary and non-limiting embodiments, the polyurethane latex polymers may be chosen from film-forming and non-film-forming polyurethane latex polymers, such as aqueous polyurethane dispersions comprising the reaction products of (i), (ii), and/or (iii), defined below.

Reaction product (i) may be any prepolymer according to the formula:

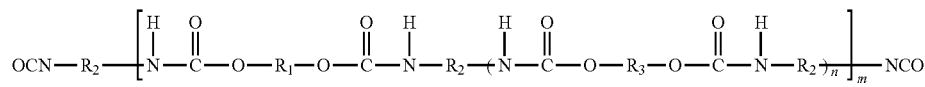

wherein R1 is chosen from bivalent radicals of a dihydroxyl functional compound, R2 is chosen from hydrocarbon radicals of an aliphatic or cycloaliphatic polyisocyanate, and R3 is chosen from radicals of a low molecular weight diol, optionally substituted with ionic groups, n ranges from about 0 to about 5, and m is greater than about 1.

Suitable dihydroxyl compounds for providing the bivalent radical R1 include those having at least two hydroxy groups, and having number average molecular weights ranging from about 700 to about 16,000, such as, for example, from about 750 to about 5000. Non-limiting examples of the high molecular weight compounds include polyester polyols, polyether polyols, polyhydroxy polycarbonates, polyhydroxy polyacetals, polyhydroxy polyacrylates, polyhydroxy polyester amides, polyhydroxy polyalkadienes and polyhydroxy polythioethers. In various embodiments, polyester polyols, polyether polyols, and polyhydroxy polycarbonates may be chosen. Mixtures of such compounds are also within the scope of the disclosure.

The polyester diol(s) may optionally be prepared from aliphatic, cycloaliphatic, or aromatic dicarboxylic or polycarboxylic acids, or anhydrides thereof; and dihydric alcohols such as diols chosen from aliphatic, alicyclic, or aromatic diols.

The aliphatic dicarboxylic or polycarboxylic acids may be chosen from, for example: succinic, fumaric, glutaric, 2,2-dimethylglutaric, adipic, itaconic, pimelic, suberic, azelaic, sebacic, maleic, malonic, 2,2-dimethylmalonic, nonanedicarboxylic, decanedicarboxylic, dodecanedioic, 1,3-cyclohexanedicarboxylic, 1,4-cyclohexanedicarboxylic, 2,5-norboranedicarboxylic, diglycolic, thiodipropionic, 2,5-naphthalenedicarboxylic, 2,6-naphthalenedicarboxylic, phthalic, terephthalic, isophthalic, oxanic, o-phthalic, tetrahydrophthalic, hexahydrophthalic or trimellitic acid.

The acid anhydrides may, in further exemplary embodiments, be chosen from o-phthalic, trimellitic or succinic acid anhydride or a mixture thereof. By way of non-limiting example only, the dicarboxylic acid may be adipic acid.

The dihydric alcohols may be chosen from, for example, ethanediol, ethylene glycol, diethylene glycol, triethylene glycol, trimethylene glycol, tetraethylene glycol, 1,2-propanediol, dipropylene glycol, tripropylene glycol, tetrapropylene glycol, 1,3-propanediol, 1,4-butanediol, 1,3-butanediol, 2,3-butanediol, 1,5-pentanediol, 1,6-hexanediol, 2,2-dimethyl-1,3-propanediol, 1,4-dihydroxycyclohexane, 1,4-dimethylolcyclohexane, cyclohexanedimethanol, 1,8-octanediol, 1,10-decanediol, 1,12-dodecanediol, neopentyl glycol, and mixtures thereof. The cycloaliphatic and/or aromatic dihydroxyl compounds may also be suitable as the dihydric alcohol(s) for the preparation of the polyester polyol(s).

The polyester diols may also be chosen from homopolymers or copolymers of lactones, which are, in at least certain embodiments, obtained by addition reactions of lactones or lactone mixtures, such as butyrolactone, ε-caprolactone and/or methyl-ε-caprolactone with the appropriate polyfunctional, e.g. difunctional, starter molecules such as, for example, the dihydric alcohols mentioned above. The corresponding polymers of ε-caprolactone may be chosen in at least some embodiments.

The polyester polyol, e.g. polyester diol, radical R1, may be obtained by polycondensation of dicarboxylic acids, such as adipic acid, with polyols, e.g. diols, such as hexanediol, neopentyl glycol, and mixtures thereof.

The polycarbonates containing hydroxyl groups comprise those known per se, such as the products obtained by reacting diols, such as (1,3)-propanediol, (1,4)-butanediol and/or (1,6)-hexanediol, diethylene glycol, triethylene glycol, or tetraethylene glycol with diaryl carbonates, for example diphenyl carbonate or phosgene.

Optional polyether polyols may be obtained in any known manner by reacting starting compounds which contain reactive hydrogen atoms with alkylene oxides, such as, for example, ethylene oxide; propylene oxide; butylene oxide; styrene oxide; tetrahydrofuran; or epichlorohydrin, or with mixtures of these alkylene oxides. In at least certain embodiments, the polyethers do not contain more than about 10% by weight of ethylene oxide units. For example, polyethers obtained without addition of ethylene oxide may be chosen.

Polyethers modified with vinyl polymers are also suitable according to various embodiments of the disclosure. Products of this type may be obtained by polymerization, for example, of styrene and acrylonitrile in the presence of polyethers, for example as described in U.S. Pat. Nos. 3,383,351; 3,304,273; 3,523,095; 3,110,695; and German patent 1 152 536.

Among the polythioethers which may be chosen include the condensation products obtained from thiodiglycol per se and/or with other glycols, dicarboxylic acids, formaldehyde, aminocarboxylic acids, and/or amino alcohols. The products obtained are either mixed polythioethers, polythioether esters, or polythioether ester amides, depending on the co-components.

Optional polyacetals include but are not limited to the compounds which may be prepared from aldehydes, for example formaldehyde, and from glycols, such as diethylene glycol, triethylene glycol, ethoxylated 4,4'-(dihydroxy)diphenyl-dimethylmethane, and (1,6)-hexanediol. Polyacetals useful according to various non-limiting embodiments of the disclosure can also be prepared by polymerization of cyclic acetals.

Optional polyhydroxy polyesteramides and polyamines include, for example, the mainly linear condensation products obtained from saturated or unsaturated, polybasic carboxylic acids or anhydrides thereof, and from saturated or unsaturated, polyvalent amino alcohols, from diamines, or from polyamines, as well as mixtures thereof.

Optional monomers for the production of polyacrylates having hydroxyl functionality comprise acrylic acid, methacrylic acid, crotonic acid, maleic anhydride, 2-hydroxyethyl acrylate, 2-hydroxyethyl methacrylate, 2-hydroxypropyl acrylate, 2-hydroxypropyl methacrylate, 3-hydroxypropyl acrylate, 3-hydroxypropyl methacrylate, glycidyl acrylate, glycidyl methacrylate, 2-isocyanatoethyl acrylate, and 2-isocyanatoethyl methacrylate.

Mixtures of dihydroxy compounds can also be chosen.

Optional polyisocyanates for providing the hydrocarbon-based radical R2 include, for example, organic diisocyanates having a molecular weight ranging from about 100 to about 1500, such as about 112 to about 1000, or about 140 to about 400.

Optional diisocyanates are those chosen from the general formula $R_2(NCO)_2$, in which $R_2$ represents a divalent aliphatic hydrocarbon group comprising from about 4 to 18 carbon atoms, a divalent cycloaliphatic hydrocarbon group comprising from about 5 to 15 carbon atoms, a divalent aralphatic hydrocarbon group comprising from about 7 to 15 carbon atoms, or a divalent aromatic hydrocarbon group comprising from about 6 to 15 carbon atoms. Examples of the organic diisocyanates which may be chosen include, but are not limited to, tetramethylene diisocyanate, 1,6-hexamethylene diisocyanate, dodecamethylene diisocyanate, cyclohexane-1,3-diisocyanate and cyclohexane-1,4-diisocyanate, 1-isocyanato-3-isocyanatomethyl-3,5,5-trimethylcyclohexane (isophorone diisocyanate or IPDI), bis(4-isocyanatocyclohexyl)-methane, 1,3-bis(isocyanatomethyl)cyclohexane and 1,4-bis(isocyanatomethyl)cyclohexane and bis(4-isocyanato-3-methylcyclohexyl)methane. Mixtures of diisocyanates can also be used.

In at least certain embodiments, diisocyanates are chosen from aliphatic and cycloaliphatic diisocyanates. For example, 1,6-hexamethylene diisocyanate, isophorone diisocyanate, and dicyclohexylmethane diisocyanate, as well as mixtures thereof may be chosen.

The use of diols, for example low molecular weight diols, R3, may in at least certain embodiments allow a stiffening of the polymer chain. The expression "low molecular weight diols" means diols having a molecular weight ranging from about 50 to about 800, such as about 60 to 700, or about 62 to 200. They may, in various embodiments, contain aliphatic, alicyclic, or aromatic groups. In certain exemplary embodiments, the compounds contain only aliphatic groups. The diols that may be chosen may optionally have up to about 20 carbon atoms, and may be chosen, for example, from ethylene glycol, diethylene glycol, propane-1,2-diol, propane-1,3-diol, butane-1,4-diol, 1,3-butylene glycol, neopentyl glycol, butylethylpropanediol, cyclohexanediol, 1,4-cyclohexanedimethanol, hexane-1,6-diol, bisphenol A (2,2-bis(4-hydroxyphenyl)propane), hydrogenated bisphenol A (2,2-bis(4-hydroxycyclohexyl)-propane), and mixtures thereof. For example, R3 may be derived from neopentyl glycol.

Optionally, the low molecular weight diols may contain ionic or potentially ionic groups. Suitable low molecular weight diols containing ionic or potentially ionic groups may be chosen from those disclosed in U.S. Pat. No. 3,412,054. In various embodiments, compounds may be chosen from dimethylol-butanoic acid (DMBA), dimethylolpropionic acid (DMPA), and carboxyl-containing caprolactone polyester diol. If low molecular weight diols containing ionic or potentially ionic groups are chosen, they may, for example, be used in an amount such that less than about 0.30 meq of —COOH is present per gram of polyurethane in the polyurethane dispersion. In at least certain exemplary and non-limiting embodiments, the low molecular weight diols containing ionic or potentially ionic groups are not used.

Reaction product (ii) may be chosen from at least one chain extender according to the formula:

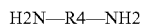

wherein R4 is chosen from alkylene or alkylene oxide radicals, said radicals not being substituted with ionic or potentially ionic groups.

Reaction product (ii) may optionally be chosen from alkylene diamines, such as hydrazine, ethylenediamine, propylenediamine, 1,4-butylenediamine and piperazine; and alkylene oxide diamines such as dipropylamine diethylene glycol (DPA-DEG available from Tomah Products, Milton, Wis.), 2-methyl-1,5-pentanediamine (Dytec A from DuPont), hexanediamine, isophoronediamine, and 4,4-methylenedi(cyclohexylamine), and the DPA-series of ether amines available from Tomah Products, Milton, Wis., including dipropylamine propylene glycol, dipropylamine dipropylene glycol, dipropylamine tripropylene glycol, dipropylamine poly(propylene glycol), dipropylamine ethylene glycol, dipropylamine poly(ethylene glycol), dipropylamine 1,3-propanediol, dipropylamine 2-methyl-1,3-propanediol, dipropylamine 1,4-butanediol, dipropylamine 1,3-butanediol, dipropylamine 1,6-hexanediol and dipropylamine cyclohexane-1,4-dimethanol, and mixtures thereof.

Reaction product (iii) may be chosen from at least one chain extender according to the formula:

wherein R5 is chosen from alkylene radicals substituted with ionic or potentially ionic groups. In at least certain exemplary embodiments, the compounds may have an ionic or potentially ionic group and two isocyanate-reactive groups.

As used herein, ionic or potentially ionic groups may include groups comprising ternary or quaternary ammonium groups, groups convertible into such groups, carboxyl groups, carboxylate groups, sulphonic acid groups, and sulphonate groups. At least partial conversion of the groups convertible into salt groups of the type mentioned may take place before or during the mixing with water. Specific compounds include diaminosulphonates, such as for example the sodium salt of N-(2-aminoethyl)-2-aminoethanesulphonic acid (AAS) or the sodium salt of N-(2-aminoethyl)-2-aminopropionic acid.

In at least certain embodiments, R5 represents an alkylene radical substituted with sulphonic acid or sulphonate groups. By way of example only, the compound is chosen from sodium salts of N-(2-aminoethyl)-2-aminoethanesulphonic acid.

By way of non-limiting example, such latexes include, but are not limited to, aqueous polyurethane dispersions comprising a reaction product of a prepolymer such as, for example, those sold under the BAYCUSAN® name by Bayer such as, for example, BAYCUSAN® C1000 (INCI name: Polyurethane-34), BAYCUSAN® C1001 (INCI name: Polyurethane-34), BAYCUSAN® C1003 (INCI name: Polyurethane-32), BAYCUSAN® C1004 (INCI name: Polyurethane-35) and BAYCUSAN® C1008 (INCI name: Polyurethane-48). In various exemplary embodiments, polyurethane latexes may be chosen from, but are not limited to, aqueous polyurethane dispersion of Isophthalic Acid/Adipic Acid/Hexylene Glycol/Neopentyl glycol/Dimethylolpropanoic Acid/Isophorone Diisocyanate copolymer (INCI name: Polyurethane-1, such as LUVISET® P.U.R, BASF), polycarbonate polyurethane, aliphatic polyurethane and aliphatic polyester polyurethane (such as the NEOREZ® series, DSM, such as NEOREZ® R989, INCI name: Polycarbamyl Polyglycon Ester). In at least one exemplary embodiment, the polyurethane latex may be chosen from Polyurethane-2 (and) Polymethyl Methacrylate sold under the tradename HYBRIDUR 875 (Air Products).

In at least certain embodiments, at least two latex polymers may be chosen from polyacrylic latex, polyacrylate latex, polystyrene latex, polyester latex, polyamide latex, polyurea latex, polyurethane latex, epoxy resin latex, cellulose-acrylate latex, and their copolymers.

In various exemplary embodiments according to the disclosure, the at least one latex may be chosen from polymers that comprise both acrylate and polyurethane parts at the molecular level.

Silicone Latex Polymers

In various exemplary and non-limiting embodiments, the silicone latex polymers may be chosen from film-forming and non-film-forming silicone latex polymers. In various exemplary embodiments, the at least one silicone latex polymer may be chosen from polymethylsiloxane resins, linear block copolymers (or linear block silicone copolymers), and mixtures thereof.

Optionally, the at least one silicone latex polymer is nonionic.

In certain embodiments, the at least one silicone latex polymer is not prepared from acrylic acid monomers or acrylate ester monomers.

In other embodiments, the at least one silicone latex polymer is nonionic and is not prepared from acrylic acid monomers or acrylate ester monomers.

1. Polymethylsiloxane Resins

According to various exemplary embodiments, the polymethylsiloxane resins may optionally be in the form of an emulsion. For example, in one exemplary and non-limiting embodiment, a polymethylsiloxane resin may be in an aqueous emulsion medium, and present in the emulsion with a solid content of about 43% by weight, based on the weight of the emulsion. An example of an exemplary polymethylsiloxane resin emulsion is the material known by the trade name BLUESIL BP 9878, commercially available from the company Bluestar Silicones.

2. Linear Block Silicone Copolymers

The linear block silicone copolymers may, in various embodiments, be chosen from uncrosslinked block copolymers which are obtained by chain extension and not by crosslinking.

The term "block copolymer" (or "sequential copolymer") denotes a polymer comprising at least two distinct blocks (sequences). Each block of the polymer results from one type of monomer or from several types of different monomers. This means that each block can be composed of a homopolymer or of a copolymer, it being possible for this copolymer constituting the block to be in its turn a random or alternating copolymer.

The linear block silicone copolymer used in the composition according to the invention optionally comprises at least two distinct silicone blocks, each block of the polymer resulting from one type of silicone monomer or from several types of different silicone monomers, such as mentioned below.

As described herein, the block silicone copolymer is "linear"; in other words, the structure of the polymer is substantially neither branched, star-branched, or grafted.

The linear block silicone copolymer may be provided in the form of particles in dispersion in an aqueous medium.

The aqueous dispersion of block copolymer particles is a silicone-in-water (Sil/W) emulsion, the oily globules of which are composed of a silicone of high viscosity, so that these globules appear to form as "soft particles".

The size of the linear block silicone copolymer particles can vary widely. For example, according to one embodiment, the linear block silicone copolymer particles may exhibit a number-average size of less than or equal to 2 microns, such as less than or equal to 1 micron.

The aqueous dispersions of linear block silicone copolymer particles used in the composition according to the invention can be chosen, for example, from those described in the document EP-A-874 017. According to this document, it is possible in particular to obtain the silicone copolymers constituting these particles by a chain extension reaction in the presence of a catalyst, starting from at least:

(i) one polysiloxane (i) having at least one reactive group, for example one or two reactive groups per molecule; and (ii) one organosilicone compound (ii) which reacts with the polysiloxane (i) by a chain extension reaction.

In various embodiments, the polysiloxane (i) is chosen from the compounds of formula (I):

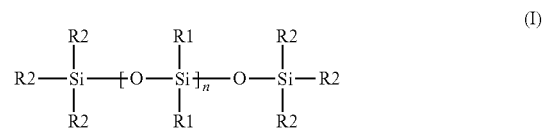

wherein R1 and R2 represent, independently of one another, a hydrocarbon group having from 1 to 20 carbon atoms and preferably from 1 to 10 carbon atoms, such as methyl, ethyl, propyl or butyl, or an aryl group, such as phenyl, or a reactive group, and n is an integer greater than 1, provided that there are on average between one and two reactive groups per polymer.

The term "reactive group" is understood to mean any group capable of reacting with the organosilicone compound (ii) to form a block copolymer. Mention may be made, as reactive groups, of hydrogen; aliphatically unsaturated groups, and in particular vinyl, allyl or hexenyl groups; the hydroxyl group; alkoxy groups, such as methoxy, ethoxy or propoxy groups; alkoxy-alkoxy groups; the acetoxy group; amino groups, and mixtures thereof. In various exemplary embodiments, more than 90 percent, such as more than 98 percent, of reactive groups are at the chain end, that is to say that the R2 radicals generally constitute more than 90 percent and even more than 98 percent of the reactive groups. Additionally, n can be an integer ranging from 2 to 100, such as from 10 to 30 or from 15 to 25.

The polysiloxanes of formula (I) are linear polymers, that is to say comprising few branchings and generally less than 2 mole percent of siloxane units. Furthermore, the R1 and R2 groups can optionally be substituted by amino groups, epoxy groups or sulfur-comprising, silicon-comprising or oxygen-comprising groups.

In one exemplary embodiment, at least 80 percent of the R1 groups are alkyl groups, for example methyl groups.

In a further embodiment, the reactive group R2 at the chain end is an aliphatically unsaturated group, for example a vinyl group.

Mention may in particular be made, as polysiloxanes (i), of dimethylvinylsiloxy-polydimethylsiloxane, a compound of formula (I) in which the R1 radicals are methyl radicals and the R2 radicals at the chain end are vinyl radicals while the other two R2 radicals are methyl radicals.

The organosilicone compound (ii) can be chosen from polysiloxanes of formula (I) or compounds acting as chain-extending agent. If it is a compound of formula (I), the polysiloxane (i) will comprise a first reactive group and the organosilicone compound (ii) will comprise a second reactive group which will react with the first. If it is a chain-extending agent, it can be a silane, a siloxane (disiloxane or trisiloxane) or a silazane. According to at least one exemplary embodiment, the organosilicone compound (ii) is a liquid organohydropolysiloxane of formula (II):

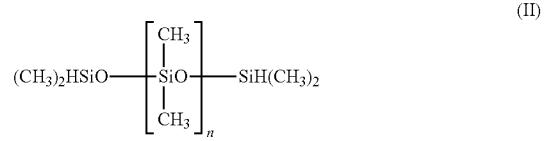

wherein n is an integer greater than 1, for example greater than 10, such as ranging from 2 to 100, from 10 to 30 or from 15 to 25. According to one embodiment, n is equal to 20.

The linear block silicone copolymers used according to the invention may optionally be devoid of oxyalkylene group(s), for example oxyethylene and/or oxypropylene group(s).

The catalyst of the reaction between the polysiloxane and the organosilicone compound can be chosen from metals, such as platinum, rhodium, tin, titanium, copper and lead. In one embodiment, the catalyst is platinum. In a further embodiment, the catalyst is rhodium.

The dispersion of linear block silicone copolymer particles used according to embodiments of the disclosure can be obtained, for example, by mixing (1) water, (2) at least one emulsifier, (3) the polysiloxane (i), (4) the organosilicone compound (ii) and (5) a catalyst. Optionally, one of the constituents (3), (4) or (5) is added last to the mixture, in order for the chain-extending reaction to begin only in the dispersion.

Mention may be made, as emulsifiers capable of being used in the preparation process described above in order to obtain the aqueous dispersion of silicone particles, of non-ionic or ionic (anionic, cationic or amphoteric) emulsifiers. They are optionally non-ionic emulsifiers which can be chosen from polyalkylene glycol ethers of fatty alcohol comprising from 8 to 30 carbon atoms and preferably from 10 to 22 carbon atoms; polyoxyalkylenated and in particular polyoxyethylenated sorbitan alkyl esters, where the alkyl radical comprises from 8 to 30 carbon atoms and preferably from 10 to 22 carbon atoms; polyoxyalkylenated and in particular polyoxyethylenated alkyl esters, where the alkyl radical comprises from 8 to 30 carbon atoms and preferably from 10 to 22 carbon atoms; polyethylene glycols; polypropylene glycols; diethylene glycols; and mixtures thereof. The amount of emulsifier(s) may range from 1 percent to 30 percent by weight, including all ranges and subranges therebetween, based on the total weight of the reaction mixture.

The emulsifier used to obtain the aqueous dispersion of particles is optionally chosen from polyethylene glycol ethers of fatty alcohols and mixtures thereof and in particular polyethylene glycol ethers of alcohols comprising 12 or 13 carbon atoms and from 2 to 100 oxyethylene units and preferably from 3 to 50 oxyethylene units, and mixtures thereof. Mention may be made, for example, of $C_{12}$-$C_{13}$ Pareth-3, $C_{12}$-$C_{13}$ Pareth-23 and mixtures thereof.

According to one exemplary embodiment, the dispersion of silicone copolymer particles may be obtained from dimethylvinylsiloxy-polydimethylsiloxane (or divinyldimethicone), as compound (i), and from the compound of formula (II), optionally with n=20, as compound (ii), optionally in the presence of a catalyst of platinum type, and the dispersion of particles may be obtained in the presence of $C_{12}$-$C_{13}$ Pareth-3 and $C_{12}$-$C_{13}$ Pareth-23, as emulsifiers.

By way of example, as dispersion of silicone copolymer particles, the product sold under the name HMW 2220 by Dow Corning may be chosen (CTFA name: divinyldimethicone/dimethicone copolymer/$C_{12}$-$C_{13}$ Pareth-3/$C_{12}$-$C_{13}$ Pareth-23), which is a 60 percent aqueous dispersion of divinyldimethicone/dimethicone copolymer and comprising $C_{12}$-$C_{13}$ Pareth-3 and $C_{12}$-$C_{13}$ Pareth-23, said dispersion comprising approximately 60 percent by weight of copolymer, 2.8 percent by weight of $C_{12}$-$C_{13}$ Pareth-23, 2 percent by weight of $C_{12}$-$C_{13}$ Pareth-3 and 0.31 percent by weight of preservatives, the remainder to 100 percent being water.

Oil Phase

The oil phase of the O/W emulsion comprises at least one water-insoluble component. The at least one water-insoluble component may, according to various embodiments, be present in the emulsion in an amount ranging up to about 50% by weight of active material, relative to the total weight of the emulsion, such as, for example, up to about 45%, up to about 40%, up to about 35%, up to about 30%, up to about 25%, or up to about 20%. By way of non-limiting example, the water-insoluble component may be present in an amount ranging from about 0.01% to about 40%, about 0.1% to about 35%, about 0.5% to about 30%, about 1% to about 25%, about 2% to about 20%, about 2% to about 12%, or about 3% to about 10%, such as about 4% to about 6%, by weight of active material, relative to the total weight of the emulsion.

Water-insoluble components may include, for example, oils such as volatile oils and non-volatile oils, UV agents, and antioxidants, as well as combinations thereof. The at least one water-insoluble component may be of animal, plant, mineral, or synthetic origin. The particles or droplets of the at least one water-insoluble component may have a size ranging to about 50 µm, such as up to about 30 µm, or up to about 10 µm, for example from about 0.1 µm to about 15 µm.

According to at least certain exemplary and non-limiting embodiments, the at least one water-insoluble component may be chosen from oils such as hydrocarbon-based oils, silicone oils, fluoro oils, non-fluoro oils, and mixtures thereof. As used herein, the term "silicone oil" means an oil comprising at least one silicon atom, and especially at least one Si—O group, and the term "fluoro oil" means an oil comprising at least one fluorine atom. The term "hydrocarbon-based oil" means an oil mainly containing hydrogen and carbon atoms. The oils may optionally comprise oxygen, nitrogen, sulfur and/or phosphorus atoms, for example in the form of hydroxyl or acid radicals.

Volatile Oils

As described herein, the at least one water-insoluble component may be chosen from one or more volatile oils. The term "volatile oil" means any non-aqueous medium that is capable of evaporating on contact with the skin or the lips in less than one hour, at room temperature and atmospheric pressure. The volatile oil may be a cosmetic volatile oil, which is liquid at room temperature. For example, a volatile oil may have an evaporation rate ranging from 0.01 to about 200 mg/cm2/min.

Exemplary volatile oils useful according to various embodiments include hydrocarbon-based oils containing from 8 to 16 carbon atoms, and especially C8-C16 branched alkanes (also known as isoparaffins), for instance isododecane (also known as 2,2,4,4,6-pentamethylheptane), isodecane and isohexadecane, for instance the oils sold under the trade names Isopar® or Permethyl®.

Volatile oils that may also be used include volatile silicones, for instance volatile linear or cyclic silicone oils, especially those with a viscosity of less than or equal to 8 centistokes (cSt) (8×10-6 m2/s), and especially containing from 2 to 10 silicon atoms and in particular from 2 to 7 silicon atoms, these silicones optionally comprising alkyl or alkoxy groups containing from 1 to 10 carbon atoms. As volatile silicone oils that may be used in the invention, mention may be made especially of dimethicones with viscosities of 5 and 6 cSt, octamethylcyclotetrasiloxane, decamethyl-cyclopentasiloxane, dodecamethylcyclohexasiloxane, heptamethylhexyltrisiloxane, heptamethyloctyltrisiloxane, hexamethyldisiloxane, octamethyltrisiloxane, decamethyl-tetrasiloxane and dodecamethylpentasiloxane, and mixtures thereof.

Non-Volatile Oils

As described herein, the at least one water-insoluble component may be chosen from one or more non-volatile oils. The term "non-volatile oil" means an oil that remains on the skin at room temperature and atmospheric pressure. For example, a non-volatile oil has an evaporation rate less than 0.01 mg/cm2/min.

Exemplary non-volatile oils useful according to various embodiments include non-volatile hydrocarbon-based, fluoro and/or silicone oils. Non-volatile hydrocarbon-based oils may be chosen from, for example, hydrocarbon-based oils of animal origin, such as perhydrosqualene; hydrocarbon-based oils of plant origin, such as phytostearyl esters, such as phytostearyl oleate, phytostearyl isostearate and lauroyl/octyldodecyl/phytostearyl glutamate (Ajinomoto, Eldew PS203), triglycerides formed from fatty acid esters of glycerol, in particular in which the fatty acids may have chain lengths ranging from $C_4$ to $C_{36}$ and especially from $C_{18}$ to $C_{36}$, these oils possibly being linear or branched, and saturated or unsaturated; these oils may especially be heptanoic or octanoic triglycerides, shea oil, alfalfa oil, poppy oil, winter squash oil, millet oil, barley oil, quinoa oil, rye oil, candlenut oil, passionflower oil, shea butter, aloe vera oil, sweet almond oil, peach stone oil, groundnut oil, argan oil, avocado oil, baobab oil, borage oil, broccoli oil, calendula oil, camelina oil, canola oil, carrot oil, safflower oil, flax oil, rapeseed oil, cotton oil, coconut oil, marrow seed oil, wheatgerm oil, jojoba oil, lily oil, macadamia oil, corn oil, meadowfoam oil, St John's Wort oil, monoi oil, hazelnut oil, apricot kernel oil, walnut oil, olive oil, evening primrose oil, palm oil, blackcurrant pip oil, kiwi seed oil, grapeseed oil, pistachio oil, winter squash oil, pumpkin oil, musk rose oil, sesame oil, soybean oil, sunflower oil, castor oil and watermelon seed oil, and mixtures thereof, or alternatively caprylic/capric acid triglycerides, such as those sold by the company Stearineries Dubois or those sold under the names Miglyol® 810, 812 and 818 by the company Dynamit Nobel; or linear or branched hydrocarbons of mineral or synthetic origin, such as liquid paraffins and derivatives thereof, petroleum jelly, polydecenes, polybutenes, hydrogenated polyisobutene such as Parleam, and squalane.

Non-volatile oils may also be chosen from, for example, synthetic ethers containing from 10 to 40 carbon atoms or oils of high molar mass, in particular having a molar mass ranging from about 400 to about 10 000 g/mol, in particular from about 650 to about 10 000 g/mol, in particular from about 750 to about 7500 g/mol and more particularly ranging from about 1000 to about 5000 g/mol. As oils of high molar mass that may be used in the present invention, mention may especially be made of oils chosen from lipophilic polymers, silicone oils, oils of plant origin, and mixtures thereof.

As additional exemplary non-volatile oils, optionally partially hydrocarbon-based and/or silicone fluoro oils, for instance fluorosilicone oils, fluoropolyethers and fluorosilicones as described in document EP-A-847 752, and silicone oils, for instance linear or cyclic non-volatile polydimethylsiloxanes (PDMS); polydimethylsiloxanes comprising alkyl, alkoxy or phenyl groups, which are pendant or at the end of a silicone chain, these groups containing from 2 to 24 carbon atoms; phenyl silicones, for instance phenyl trimethicones, phenyl dimethicones, phenyl trimethylsiloxy diphenyl siloxanes, diphenyl dimethicones, diphenyl methyldiphenyl trisiloxanes and 2-phenylethyl trimethylsiloxy silicates, may be mentioned.

UV Agents

As described herein, the at least one water-insoluble component may be chosen from one or more UV agents. The UV agents may be chosen from organic UV agents. As used herein, the term "UV agent" is intended to include sunscreen agents and UV filters.

Organic UV agents may, for example, be chosen from water-soluble organic screening agents, fat-soluble organic screening agents, or agents which are insoluble in the solvents included in suntan products, and mixtures thereof.

The organic UV agents may, for example, be chosen from cinnamic derivatives; anthranilates; salicylic derivatives; dibenzoylmethane derivatives; camphor derivatives; benzophenone derivatives; β,β-diphenylacrylate derivatives; triazine derivatives; benzotriazole derivatives; benzalmalonate derivatives; benzimidazole derivatives; imidazolines; bis-benzazolyl derivatives; p-aminobenzoic acid (PABA) derivatives; methylenebis(hydroxyphenylbenzotriazole) derivatives; benzoxazole derivatives; screening polymers and screening silicones; α-alkylstyrene-derived dimers; 4,4-diarylbutadienes; merocyanin derivatives; and mixtures thereof.

Examples of complementary organic photoprotective agents include those denoted hereinbelow under their INCI name:

Cinnamic Derivatives: Ethylhexyl Methoxycinnamate marketed in particular under the trademark "Parsol MCX®" by DSM Nutritional Products, Inc., Isopropyl Methoxycinnamate, Isoamyl p-Methoxycinnamate marketed under the trademark "Neo Heliopan E 1000®" by Symrise, DEA Methoxycinnamate, Diisopropyl Methylcinnamate, Glyceryl Ethylhexanoate Dimethoxycinnamate;

Dibenzoylmethane Derivatives: Butyl Methoxydibenzoylmethane marketed especially under the trademark "Parsol 1789®" by DSM Nutritional Products, Inc., Isopropyl Dibenzoylmethane;

Para-Aminobenzoic Acid Derivatives: PABA, Ethyl PABA, Ethyl Dihydroxypropyl PABA, Ethylhexyl Dimethyl PABA marketed in particular under the trademark "Escalol 507®" by ISP, Glyceryl PABA, PEG-25 PABA marketed under the trademark "Uvinul P25®" by BASF;

Benzotriazole derivatives, in particular, phenylbenzotriazole derivatives: Drometrizole trisiloxane, marketed under the trademark "Silatrizole" by Rhodia Chimie or "Mexoryl XL" by L'Oreal;

Salicylic Derivatives: Homosalate marketed under the trademark "Eusolex HMS®" by Merck KGaA/EMD Chemicals, Inc. and EMD Chemicals Inc, Ethylhexyl Salicylate marketed under the trademark "Neo Heliopan OS®" by Symrise, Dipropylene Glycol Salicylate marketed under the trademark "Dipsal™" by Lubrizol Advanced Materials, Inc., TEA Salicylate marketed under the trademark "Neo Heliopan® TS" by Symrise;

β,β-Diphenylacrylate Derivatives: Octocrylene marketed in particular under the trademark "Uvinul N539T®" by BASF, Etocrylene marketed in particular under the trademark "Uvinul® N35" by BASF;

Benzophenone Derivatives: Benzophenone-1 marketed under the trademark "Uvinul®400" by BASF, Benzophenone-2 marketed under the trademark "Uvinul® D50" by BASF, Benzophenone-3 or Oxybenzone marketed under the trademark "Uvinul® M40" by BASF, Benzophenone-4 marketed under the trademark "Uvinul® MS40" by BASF, Benzophenone-5, Benzophenone-6 marketed under the trademark "Helisorb® 11" by Norquay, Benzophenone-8, Benzophenone-9, Benzophenone-12, n-Hexyl 2-(4-diethylamino-2-hydroxybenzoyl)benzoate marketed under the trademark "Uvinul® A+" by BASF;

Benzylidenecamphor Derivatives: 3-Benzylidenecamphor manufactured under the trademark "Mexoryl™ SD" by Chimex, 4-Methylbenzylidenecamphor marketed under the trademark "Eusolex® 6300" by Merck, Benzylidene Camphor Sulfonic acid manufactured under the trademark "Mexoryl™ SL" by Chimex, Camphor Benzalkonium Methosulfate manufactured under the trademark "Mexoryl™ SO" by Chimex, Terephthalylidene Dicamphor Sulfonic acid manufactured under the trademark "Mexoryl™ SX" by Chimex, Polyacrylamidomethyl Benzylidene Camphor manufactured under the trademark "Mexoryl™ SW" by Chimex;

Phenylbenzimidazole Derivatives: Phenylbenzimidazole Sulfonic acid marketed in particular under the trademark "Eusolex® 232" by Merck and EMD INC., Disodium Phenyl Dibenzimidazole Tetrasulfonate marketed under the trademark "Neo Heliopan® AP" by Symrise;

Phenylbenzotriazole Derivatives: Drometrizole Trisiloxane, Methylene bis(Benzotriazolyl) Tetramethylbutylphenol, or in micronized form as an aqueous dispersion under the trademark "Tinosorb® M" by BASF;

Triazine Derivatives: bis-Ethylhexyloxyphenol Methoxyphenyl Triazine marketed under the trademark "Tinosorb® S" by BASF, Ethylhexyl Triazone marketed in particular under the trademark "Uvinul® T150" by BASF, Diethylhexyl Butamido Triazone marketed under the trademark "Uvasorb® HEB" by 3V Group, 2,4,6-Tris(dineopentyl 4'-aminobenzalmalonate)-s-triazine, 2,4,6-Tris(diisobutyl 4'-aminobenzalmalonate)-s-triazine, 2,4-Bis(n-butyl 4'-aminobenzoate)-6-(aminopropyltrisiloxane)-s-triazine, 2,4-Bis(dineopentyl 4'-aminobenzalmalonate)-6-(n-butyl 4'-aminobenzoate)-s-triazine, triazine agents, especially 2,4,6-tris(biphenyl-1,3,5-triazines (in particular 2,4,6-tris(biphenyl-4-yl)-1,3,5-triazine and 2,4,6-tris(terphenyl)-1,3,5-triazine;

Anthranilic Derivatives: Menthyl anthranilate marketed under the trademark "Neo Heliopan® MA" by Symrise;

Imidazoline Derivatives: Ethylhexyl Dimethoxybenzylidene Dioxoimidazoline Propionate;

Benzalmalonate Derivatives: Polyorganosiloxane containing benzalmalonate functions, for instance Polysilicone-15, marketed under the trademark "Parsol® SLX" by DSM Nutritional Products, Inc.;

4,4-Diarylbutadiene Derivatives: 1,1-Dicarboxy(2,2'-dimethylpropyl)-4,4-diphenylbutadiene; and Benzoxazole derivatives: 2,4-Bis[5-(1-dimethylpropyl)benzoxazol-2-yl(4-phenyl)imino]-6-(2-et-hylhexyl)imino-1,3,5-triazine marketed under the trademark Uvasorb K 2A by Sigma 3V; and mixtures thereof.

According to at least certain embodiments, organic UV agents may be chosen from: Ethylhexyl Methoxycinnamate, Ethylhexyl Salicylate, Homosalate, Butyl Methoxydibenzoylmethane, Octocrylene, Phenylbenzimidazole Sulfonic Acid, Benzophenone-3, Benzophenone-4, Benzophenone-5, n-Hexyl 2-(4-diethylamino-2-hydroxybenzoyl)benzoate, 4-Methylbenzylidene camphor, Terephthalylidene Dicamphor Sulfonic Acid, Disodium Phenyl Dibenzimidazole Tetrasulfonate, Methylene bis-Benzotriazolyl Tetramethylbutylphenol, Bis-Ethylhexyloxyphenol Methoxyphenyl Triazine, Ethylhexyl Triazone, Diethylhexyl Butamido Triazone, 2,4,6-Tris(dineopentyl 4'-aminobenzalmalonate)-s-triazine, 2,4,6-Tris(diisobutyl 4'-aminobenzalmalonate)-s-triazine, 2,4-Bis(n-butyl 4'-aminobenzoate)-6-(aminopropyltrisiloxane)-s-triazine, 2,4-Bis(dineopentyl 4'-aminobenzalmalonate)-6-(n-butyl 4'-aminobenzoate)-s-triazine, 2,4,6-Tris(biphenyl-4-yl)-1,3,5-triazine, 2,4,6-Tris(terphenyl)-1,3,5-triazine, Drometrizole Trisiloxane, Polysilicone-15, 1,1-Dicarboxy(2,2'-dimethylpropyl)-4,4-diphenylbutadiene, 2,4-Bis[5-1-(dimethylpropyl)benzoxazol-2-yl(4-phenyl)imino]-6-(2-et-hylhexyl)-imino-1,3,5-triazine, and mixtures thereof.

Antioxidants

As described herein, the at least one water-insoluble component may be chosen from one or more antioxidants. Antioxidants may include, for example, enzymatic antioxidants or non-enzymatic antioxidants.

Exemplary and non-limiting enzymatic antioxidants may be chosen from hormones such as melatonin, oestrogen; primary enzymes, such as superoxide dismutase (SOD), catalase, and peroxidase; and secondary enzymes, such as glutathione, thioredoxin; and combinations thereof.

Exemplary and non-limiting non-enzymatic antioxidants may be chosen from minerals, such as copper, selenium, and zinc; vitamins, such as vitamin A, C, K, and E; carotenoids, such as tycopene, n-carotene, lycopene, lutein, and zeaxanthin; organosulfur compounds, such as indoles and alfyl sulfide; low molecular weight antioxidants, such as uric acid, lipoic acid, cysteine, and N-acetylcysteine; phenols, such as alkyl phenols, β-cyanins, capsaicinoids, hydroxybenzoketones, methoxyphenols, naphthoquinones, and phenolic terpenes; and polyphenols, as well as combinations thereof.

Polyphenols are normally available in plants and are very helpful to protect plants and also animals from usual health disorders and also the impacts of aging. Polyphenols function as potent free radical scavengers by donating their alcoholic hydrogen or one of their delocalized electrons. The two classes of polyphenols are flavonoids and non-flavonoids.

Flavonoids are a specific group of polyphenols, and are the most plentiful group of polyphenol compounds, making up about two-thirds of the total phenols in consumed feed. Over 4,000 flavonoids have been identified, many of which occur in fruits, vegetables and beverages (tea, coffee, beer, wine and fruit drinks). The flavonoids have been reported to have antiviral, anti-allergic, antiplatelet, anti-inflammatory, anti-tumor and antioxidant activities. Flavonoids protect lipids and vital cell components from damaging oxidative stress by efficiently scavenging free radicals.

Exemplary and non-limiting flavonoid compounds include: chalcones, such as phloretin, phloridzin, aspalathin, and neohesperidine; flavanols, such as catechin, fisetin, kaempferol, myricetin, quercetin, rutin, proanthocyanidins, pyroanthocyanidins, theaflavins, and thearubrins; dehydroflavonols, such as astilbin, dehydroquercetin, and silibinin; flavanones, such as hesperidin, neohesperidin, hesperetin, naringenin, naringin, and poncirin; flavones, such as apigenin, baicalin, diosmin, and rhoifolin; anthocyanins, such as cyanidin, delphinidin, malvidin, peonidin, and petunidin; tannins, such as ellagitannins, tannic acid, gallic acid, and ellagic acid; isoflavonoids, such as biochanin A, Daidzein, and Genistein; and neoflavanoids, as well as combinations thereof.

Exemplary and non-limiting non-flavonoid compounds include: Curcuminoids such as curcumin, tetrahydrocurcumin, turmerone; Stibenoids such as astringin, resveratrol, rhaponticin; Aurones such as bracteatin, aureusidin; and Lignans such as pinoresinol, as well as combinations thereof.

Other phenylpropanoids such as hydroxycinnamic acids, for example, ferulic acid, chlorogenic acid, verbascoside; hydroxybenzoic acids, for example, dodecyl, ethylhexyl, octyl propyl gallates; phenolic aldehydes; phenylpropenes; coumarins, coumestans, tyrosols.

Other phenolic compounds, in addition to polyphenols, include alkylphenols, betacyanins, capsaicinoids, hydroxybenzoketones, methoxyphenols, naphthoquinones, and phenolic terpenes. Some popular examples are ferulic acid, hydroxytyrosol, cinnamic acid, caffeic acid, and p-coumaric acid.

Surfactant

According various exemplary and non-limiting embodiments, the at least one surfactant may be chosen such that it has a hydrophilic-lipiphilic balance ("HLB") value of up to about 18, such as up to about 15, or up to about 10, such as, for example, ranging from about 3 to about 15, including all ranges and sub-ranges therebetween. In at least certain embodiments, the surfactant may be chosen to have an HLB value of approximately the same as the HLB value of the water-insoluble component of the oil phase. By "approximately the same," it is intended that, at least in some embodiments, relative to the HLB value of the water-insoluble component, the HLB value of the at least one surfactant can be +/−3, +/−2, +/−1, or +/−0.5, for example. Thus, for example, if the HLB value of the water-insoluble component is 8, the HLB value of the at least one surfactant may be chosen to be in the range of from about 5 to about 11, about 6 to about 10, about 7 to about 9, or about 7.5 to about 8.5.

In various exemplary embodiments, the surfactant is present in an amount that, in combination with the latex particles, stabilizes the emulsion. In other words, in at least certain exemplary embodiments, the amount of surfactant chosen is such that it will not, by itself, stabilize the O/W emulsion. For example, in at least one embodiment, the at least one surfactant may be present in an amount ranging up to about 10% by weight, relative to the total weight of the emulsion, such as up to about 5% by weight, up to about 4% by weight, up to about 3% by weight, or up to about 2% by weight, relative to the weight of the composition of the present invention. By way of example, the surfactant may be present in an amount ranging from about 0.1% to about 10%, such as about 0.5% to about 5%, about 0.5% to about 4%, about 0.5% to about 3%, about 0.5% to about 2%, or about 0.5% to about 1% by weight, relative to the total weight of the emulsion, including all ranges and subranges therebetween. As yet a further example, the surfactant may be present in an amount ranging from about 0.1% to about 1%, such as about 0.5%, by weight, relative to the total weight of the emulsion.

Exemplary surfactants may be chosen from charged and non-charged, anionic surfactants, nonionic surfactants, amphoteric or zwitterionic surfactants and cationic surfactants, and mixtures thereof. In various embodiments, the surfactants are chosen from non-ionic and/or anionic surfactants having an HLB value of approximately the same as the HLB value of the water-insoluble component of the oil phase.

As used herein, term "anionic surfactant" is understood to mean a surfactant comprising, as ionic or ionizable groups, only anionic groups. These anionic groups are preferably chosen from the following groups: CO2H, CO2—, SO3H, SO3—, OSO3H, OSO3—, H2PO3, —HPO3—, —PO32—, —H2PO2, =HPO2, —HPO2—, =PO2—, =POH and =PO−.

For example, anionic surfactant may be chosen from alkyl sulfates, alkyl ether sulfates, alkylamido ether sulfates, alkylaryl polyether sulfates, monoglyceride sulfates, alkylsulfonates, alkylamidesulfonates, alkylarylsulfonates, α-olefinsulfonates, paraffinsulfonates, alkyl sulfosuccinates, alkyl ether sulfosuccinates, alkylamide sulfosuccinates, alkyl sulfoacetates, acyl sarcosinates, acyl glutamates, alykyl ether carboxylates, alkyl sulfosuccinamates, acyl isethionates and N-acyl taurates; monoalkyl esters of polyglycoside-polycarboxylic acids, acyl lactylates, salts of D-galactosideuronic acids, salts of alkyl ether carboxylic acids, salts of alkylaryl ether carboxylic acids, salts of alkylamido ether carboxylic acids; and the corresponding non-salified forms of all these compounds; the alkyl and acyl groups of all these compounds comprising from 6 to 24 carbon atoms, and the aryl group denoting a phenyl group.

Optionally these compounds can be oxyethylenated, and if so, may comprise from 1 to 50 ethylene oxide units, such as from 1 to 10 ethylene oxide units.

Salts of C6-C24 alkyl monoesters of polyglycoside-polycarboxylic acids can be chosen from C6-C24 alkyl polyglycoside-citrates, C6-C24 alkyl polyglycoside-tartrates and C6-C24 alkyl polyglycoside-sulfosuccinates. Acyl lactylates may optionally have an acyl group comprising from 8 to 20 carbon atoms.

According to exemplary embodiments, the anionic surfactant may be in the salt form, and may be chosen from alkali metal salts, such as the sodium salt or potassium salt, the ammonium salt, the amine salts, the aminoalcohol salts, or the alkaline earth metal salts, such as the magnesium salt.

In at least certain exemplary embodiments, the anionic surfactants are chosen from (C6-24)alkyl sulfates, (C6-24) alkyl ether sulfates, acyl glutamates and (C6-C24)alkyl ether carboxylates, such as in the form of alkali metal, ammonium, aminoalcohol or alkaline earth metal salts, or a mixture of these compounds. In yet further embodiments, the anionic surfactants are chosen from (C12-20)alkyl sulfates, (C12-20)alkyl ether sulfates comprising from 2 to 20 ethylene oxide units, acyl glutamates or (C12-C20)alkyl ether carboxylates, such as in the form of alkali metal, ammonium, aminoalcohol and alkaline earth metal salts, or a mixture of these compounds.

Exemplary and non-limiting non-ionic surfactants include polyethoxylated and/or polypropoxylated alkyl phenols, alpha-diols and alcohols, comprising fatty chains comprising, for example, from 8 to 18 carbon atoms, and the number of ethylene oxide and/or propylene oxide groups may range from 2 to 50. The at least one non-ionic surfactant may be chosen, for example, from copolymers of ethylene oxide and of propylene oxide, condensates of ethylene oxide and/or of propylene oxide with fatty alcohols; polyethoxylated fatty amides comprising, for example, from 2 to 30 mol of ethylene oxide, polyglycerolated fatty amides comprising on average 1 to 5, and, for example, 1.5 to 4, glycerol groups; polyethoxylated fatty amines comprising, for example, from 2 to 30 mol of ethylene oxide; oxyethylenated fatty acid esters of sorbitan comprising, for example, from 2 to 30 mol of ethylene oxide; fatty acid esters of sucrose, fatty acid esters of polyethylene glycol, alkylpolyglycosides, N-alkylglucamine derivatives, and amine oxides such as (C10-C14) alkyl amine oxides and N-acylaminopropylmorpholine oxides.

Exemplary and non-limiting amphoteric or zwitterionic surfactants include derivatives of optionally quaternized secondary or tertiary aliphatic amines comprising at least one anionic group, such as, for example, a carboxylate, sulfonate, sulfate, phosphate or phosphonate group, and in which the aliphatic group or at least one of the aliphatic groups is a linear or branched chain comprising from 8 to 22 carbon atoms.

For example, (C8-C20)alkyl betaines, sulfobetaines, (C8-C20)alkylamido(C1-C6)alkyl betaines, such as cocoamidopropyl betaine, or (C8-C20)alkylamido(C1-C6)alkyl sulfobetaines, may be chosen. As further examples, optionally quaternized secondary or tertiary aliphatic amines such as disodium cocoamphodiacetate, disodium lauroamphodiacetate, disodium caprylamphodiacetate, disodium caprylamphodiacetate, disodium cocoamphodi-propionate, disodium lauroamphodipropionate, disodium caprylamphodipropionate, disodium caprylamphodipropionate, lauroamphodipropionic acid and co-coampho⌐dipropionic acid may be chosen. As yet further examples, cocoamphodiacetate sold by Rhodia under the trade name Miranol® C2M Concentrate or the compound under the name sodium diethylaminopropyl cocoaspartamide and sold by Chimex under the name Chimexane HB may be chosen.

In at least certain embodiments, the amphoteric or zwitterionic surfactants are chosen from (C8-C20)alkyl betaines, (C8-C20)alkylamido(C1-C6)alkyl betaines and (C8-C20) alkylamphodiacetates, and also the sodium salt of diethyl-aminopropyl lauryla-minosuccinamate, and mixtures thereof are chosen. In various embodiments, the surfactants may be chosen from cocoylamidopropyl betaine, cocoyl betaine, and cocoamphodiacetate, individually, or may be chosen as a mixture thereof of two or all three.

Non-limiting example of cationic surfactants include salts of optionally polyoxyalkylenated primary, secondary and tertiary fatty amines; quaternary ammonium salts such as tetra alkyl ammonium, alkylamidoalkyltrialkyl ammonium, trialkylbenzyl ammonium, trialkylhydroxyalkyl ammonium and alkylpyridinium chlorides and bromides; imidazoline derivatives; and cationic amine oxides.

Methods of Making an Emulsion

As disclosed herein, stable O/W emulsions can be prepared by providing latex film forming polymer particles at the interface of the aqueous phase and the oil phase, without forming a continuous closed capsule around the oily particle or droplet. The O/W emulsion may further comprise at least one surfactant, but as stated herein, the amount of the at least one surfactant is not, in at least certain embodiments, sufficient to stabilize the O/W emulsion by itself, as the latex particles serve to provide stabilization in addition to that provided by the surfactant.

According to various embodiments, the O/W emulsions can be prepared by any appropriate method. In at least one embodiment, the emulsion is prepared by first mixing the aqueous phase comprising the latex particles and the oil phase, and then subjecting the mixture to homogenization, for example either low- or high-pressure homogenization. In yet a further embodiment, the emulsion is prepared by combining all components into a low- or high-pressure homogenizer and homogenizing the components. In certain embodiments, the mixture or O/W emulsion can be subjected to the homogenization process more than once, such as from 2 to 10 times, in the process of preparing the emulsion.

As used herein, the term "low-pressure homogenizer" and variations thereof is intended to denote the use of a homogenizer operating under a pressure ranging up to about 150 bar, such as up to about 100 bar. As used herein, "high-pressure homogenizer" and variations thereof is intended to denote use of a homogenizer operating under a pressure ranging from about 100 to about 1000 bar, for example from about 250 bar to about 850 bar, from about 400 to about 700 bar, or from about 500 to about 600 bar.

As used herein, the term "mixing" is intended to mean any process by which the components are combined in such a way as to make a mixture thereof that is substantially uniform throughout.

The homogenization process may, for example, be carried out at ambient temperature, optionally by successive passes, for example from 2 to 10 passes, under the pressure used, wherein the mixture is optionally brought back to ambient temperature between each pass.

Alternatively, or in addition, homogenization can be carried out under ultrasound.

The above exemplified methods are not intending to be limiting; rather, any method is contemplated wherein the combination of the at least one surfactant with the oil and aqueous phases can be prepared into a stable O/W emulsion.

According to various embodiments, the methods for preparing the emulsion may optionally be carried out at lower temperatures than conventional processes, which may be advantageous in at least certain embodiments.

According to various embodiments, the weight ratio of (a) the aqueous dispersion of particles of at least one of an acrylate latex, a polyurethane latex, and a silicone latex, as polymeric active material (dry weight basis), to (b) the at least one oil phase, as active material, ranges from about 10:1 to about 1:20, latex:oil, such as ranging from about 10:1 to about 1:10, about 7:1 to about 1:7, about 5:1 to about 1:5, about 3:1 to about 1:3, or about 1:1, for example from about 3:1 to about 1:5, including all ranges and sub-ranges therebetween.

According to at least certain exemplary embodiments, the emulsions prepared according to the disclosure are stable. As used herein, the terms "stable" and "stabilize," as well as variations thereof, are intended to mean that the emulsion shows no phase separation as perceptible to the human eye after one month at ambient pressure and room temperature.

Compositions

As described herein, hair styling and/or shaping compositions comprising the O/W emulsions according to the disclosure are contemplated. Hair treated with compositions according to the disclosure may exhibit good styling properties (e.g. high humidity curl retention, anti-frizz, and/or good curl definition) with additional conditioning effects (e.g. may impart shine, softness, moisturizing effects, and/or be non-greasy).

The latex polymers in said O/W emulsions may be in unneutralized or partially unneutralized form. In various embodiments, the compositions may comprise additional components in addition to the O/W emulsion. For example, the compositions may comprise at least one solvent. The at least one solvent may be chosen from water, at least one cosmetically acceptable organic solvent, or a mixture of water and at least one cosmetically acceptable organic solvent. Cosmetically acceptable organic solvents may, in various embodiments, be water-miscible, e.g. a mixture capable of forming at 25° C. a homogeneous mixture that is transparent, or substantially transparent, to the eye. For instance, cosmetically acceptable organic solvents may be chosen from lower monoalcohols, such as those containing from about 1 to 5 carbon atoms, for example ethanol and isopropanol; polyols, including glycols, such as those containing from about 2 to 8 carbon atoms, for example propylene glycol, ethylene glycol, 1,3-butylene glycol, dipropylene glycol, hexylene glycol, and glycerin; hydrocarbons, such as, for example, isododecane and mineral oil; and silicones, such as dimethicones, cyclomethicones, and cyclopentasiloxane; as well as mixtures thereof.

The at least one solvent may be present in an amount ranging up to about 95%, such as from about 1% to about 90%, from about 5% to about 80%, or from about 10% to about 60% by weight, relative to the total weight of the composition.

In at least certain exemplary embodiments, the latex polymer particles are not soluble in the solvent of the composition, and thus remain in particulate form even after evaporation of the solvent. For example, in embodiments where the composition comprises alcohol as a cosmetically acceptable organic solvent, the latex particles may remain in particulate form upon evaporation of the alcohol, such as once the composition is applied to a substrate.

Compositions according to various embodiments of the disclosure may further comprise additional components. Such components are known to those of skill in the art, or are within the ability of those of skill in the art to determine depending on the particular application, such as, for example, the particular component and/or amount thereof. Such components include, but are not limited to, wax dispersions, oils, surfactants, rheology modifiers, thickening agents, structuring agents, skin active agents, vitamins, plant extracts, and propellants, all in addition to any disclosed herein, as well as mixtures thereof.

In some embodiments, the wax dispersions that may additionally be present in the compositions of the present invention comprise: (i) particles having a volume-basis particle size distribution with peaks in the range of equal to or greater than 1 μm up to about 100 μm wherein the particles comprise at least one wax having a melting point of greater than 35° C. and optionally, an oil gellant; (ii) a surfactant mixture comprising a nonionic surfactant and an ionic surfactant; and (iii) water.

In various exemplary embodiments, the wax dispersion can be prepared with a surfactant mixture comprising nonionic and/or ionic surfactants, and following an emulsification process.

The particles comprising the wax dispersion of the present invention may be chosen from particles of natural and synthetic waxes. Natural waxes may include, for example, one or a combination of animal, vegetable/plant, mineral, or petroleum derived waxes. They are typically esters of fatty acids and long chain alcohols. Wax esters are derived from a variety of carboxylic acids and a variety of fatty alcohols. The waxes comprising the solid wax particle of the present invention may also be known as solid lipids.

Examples of waxes comprising the particles of the wax dispersion of the present invention include, but are not limited to, beeswax, hydrogentated alkyl olive esters such as hydrogenated myristyl olive ester and hydrogenated stearyl olive ester (commercially available under the trade name phytowax olive), VP/eicosene copolymer, commercially available from the supplier ISP under the tradenames, Antaron® V 220 or Ganex® V 220F, carnauba wax, candelilla wax, ouricoury wax, Japan wax, cork fibre wax or sugar cane wax, rice wax, montan wax, paraffin wax, lignite wax or microcrystalline wax, ceresin or ozokerite, palm kernel glycerides/hydrogenated palm glycerides and hydrogenated oils such as hydrogenated castor oil or jojoba oil, sugarcane, retamo, bayberry, rice bran, soy, castor, esparto, japan waxes, hydroxyoctacosanyl hydroxystearate, Chinese wax, cetyl palmitate, lanolin, shellac, and spermaceti; synthetic waxes such as those of the hydrocarbon type and polyethylene waxes obtained from the polymerization or copolymerization of ethylene, and Fischer-Tropsch® waxes, or else esters of fatty acids, such as octacosanyl stearate, glycerides which are solid at temperatures of above 35° C., silicone waxes, such as alkyl- or alkoxydimethicones having an alkyl or alkoxy chain ranging from 10 to 45 carbon atoms, poly(di)methylsiloxane esters which are solid at 30° C. and whose ester chain comprising at least 10 carbon atoms, or else di(1,1,1-trimethylolpropane) tetrastearate, which is sold or manufactured by Heterene under the name HEST® 2T-4S, and mixtures thereof.

Other examples of waxes or solid lipids include C20-40 di- and triglycerides, including those which contain unsaturated fatty acids, C20-40 fatty alcohols, C2-40 fatty amines and their compounds, and sterols. Yet further examples include Hest 2T-5E-4S, Ditrimethylolpropane tetralaurate, Koster BK-34, Fluoro Polymethylalkyl dimethylsiloxane, Blend of Dilauryl Adipate and Ditetradecyl Adipate, Astrocaryum MuruMuru Seed Butter, *Myrica Pubescens* Wax, PEG-70 Mango Glycerides, oxypropylenated lanolin wax, and hydrogenated Coco-glycerides.

Other suitable waxes include silsesquioxane resin waxes such as C30-45 alkyldimethylsilyl propylsilsesquioxane, commercially available as DOW CORNING SW-8005 C30 Resin Wax, from the company Dow Corning and such as those described in WO2005/100444.

The amount of particles present in the wax dispersion according to various exemplary embodiments may range from about 10-60%, such as about 15-50%, about 20-45%, or about 25-40%, by weight, including all ranges and subranges therebetween, based on the weight of the wax dispersion.

In various embodiments, the compositions described herein may have a pH ranging from about 2 to about 9, such as about 3 to about 8, or about 4 to about 7.

In at least certain exemplary embodiments, the compositions are in the form of hair styling compositions, in any form, such as, for example, a gel, a cream, a foam, a lotion, an emulsion, or a liquid that may be sprayed onto or otherwise applied to the hair. In various embodiments, the composition may be provided in the form of a gel, a mousse, or a spray. In at least certain embodiments, the composition may be applied to the hair by first applying to the hands, and then contacting the hair with the hands; in other embodiments, the composition may be applied directly onto the hair, such as by spraying. The compositions may, in various embodiments, be applied to the hair as a leave-on treatment.

Methods of Use

According to various exemplary embodiments, the O/W emulsion may be applied directly to a keratinous substrate, such as the hair, or may be applied to a keratinous substrate, such as the hair, after being incorporated into a composition, e.g. a hair styling and/or hair shaping composition.

According to various embodiments, methods of shaping or altering the shape of hair are provided, wherein said method involves applying onto the hair the emulsions or compositions of the present invention. The term "shaping hair" as used herein can also mean changing the configuration of hair.

In certain other embodiments, methods of styling hair are provided, wherein said method involves applying onto the hair, the emulsions of the present invention.

In various embodiments, the application of an external stimuli, such as physical force, for example, brushing or combing or running the fingers through the hair, may be desirable as part of the hair styling process. By way of example only, before, during, or after the emulsion or composition is applied to wet or dry hair, the hair may be further treated with said external stimuli. In at least certain embodiments, the hair may also be shaped or positioned as desired while exposed to external stimuli.

The above-described methods of the present invention may additionally include one or more steps of styling or shaping hair using a means for styling or shaping hair.

Thus, methods of shaping or altering the shape of hair, or styling hair, are provided, wherein said methods comprise applying onto the substrate or hair, an O/W emulsion or a composition comprising the O/W emulsion as described herein. Various exemplary methods comprise applying emulsions and/or compositions according to the disclosure to the hair (wet, dry or semi-dry), either before, during, or after styling the hair. One or more steps of treating the hair with an external stimuli, such as combing or brushing or running the fingers through the hair, before, during, or after the composition has been applied to the hair are also contemplated, as is one or more steps of styling or shaping hair using a means for styling or shaping hair.

The above-described methods of the present invention allow one to shape/re-shape or re-position the hair on the head, such as to straighten the hair, curl the hair, redefine hair curl, or volumize the hair, and to repeat the steps of said method as many times as desired and without needing to re-apply the emulsion or composition and/or re-wet the hair.

Furthermore, emulsions and/or compositions prepared according to various embodiments may provide for varying degrees of hold to be imparted to a hair style. By way of non-limiting example only, in order to obtain a spiky look to hair of a very short length, a high level of styling hold may be desirable. Or, as a further non-limiting example, in order to obtain a flowing look or to maintain hair curls for hair of medium length or longer length, a light to medium level of style hold may be desirable.

In addition, hair styled or shaped with the emulsions and/or compositions according to the disclosure may, in at least certain exemplary embodiments, be hydrophobic, and/or may appear less frizzy and/or may be less prone to breakage, relative to hair subjected to the same conditions but not having been styled or treated with a composition according to the disclosure.

It is to be understood that both the foregoing description and the following Examples are exemplary and explanatory only, and are not to be interpreted as restrictive of the disclosure. Moreover, it should be understood that various features and/or characteristics of differing embodiments herein may be combined with one another. It is therefore to be understood that numerous modifications may be made to the illustrative embodiments and that other arrangements may be devised without departing from the scope of the disclosure. Other embodiments will be apparent to those skilled in the art from consideration of the disclosure and practice of the various exemplary embodiments disclosed herein.

It is also to be understood that, as used herein the terms "the," "a," or "an," mean "at least one," and should not be limited to "only one" unless explicitly indicated to the contrary. Thus, for example, the use of "a surfactant" is intended to mean at least one surfactant.

Unless otherwise indicated, all numbers used in the specification and claims are to be understood as being modified in all instances by the term "about," whether or not so stated. The term "about" as it modifies numbers herein is meant to indicate a difference of 10% or less from the stated number, such as 9% or less, such as 8% or less, such as 7% or less, such as 6% or less, such as 5% or less, such as 4% or less, such as 3% or less, such as 2% or less, or such as 1% or less, in various exemplary embodiments. Thus, by way of example only, in one embodiment where "about" indicates a difference of 10% or less, the phrase "about 20%" is intended to encompass a range from 18%-22%. In another exemplary embodiment where "about" indicates a difference of 5% or less, the phrase "about 20%" is intended to encompass a range from 19%-21%. All such numbers within each specified range are hereby explicitly intended to be included in the disclosure.

It should also be understood that the precise numerical values used in the specification and claims form additional embodiments of the disclosure, and are intended to include any ranges or sub-ranges which may be narrowed to any two end points disclosed within the exemplary ranges and values provided, and it is also intended to include the specific end points of each range as independent values, whether or not so stated. Efforts have been made to ensure the accuracy of the numerical values disclosed herein. Any measured numerical value, however, can inherently contain certain errors resulting from the standard deviation found in its respective measuring technique.

All patents and publications are expressly incorporated herein in their entireties.

EXAMPLES

The following Examples are intended to be non-restrictive and explanatory only, with the scope of the invention being defined by the claims.

Example 1

O/W Emulsions

The O/W emulsions A-OO shown in Table 1 were made by: (i) heating the oil and the surfactants at 80° C. until homogeneous; (ii) adding the oil/surfactants solution to water at 60° C. while homogenizing at 6000 rpm until the solution cools to room temperature; (iii) adding latex and stirring for 10 minutes.

The HLB values of the oils used are: Olive Oil=7, Jojoba Oil=6, Dimethicone=5, Argan Oil=9, and Phenyl Trimethicone=8. The surfactant was a mixture of PEG-100 Stearate and Glyceryl Stearate, mixed in ratios in order to provide a surfactant mixture having an HLB value similar to the HLB value of the oil used in each sample.

TABLE 1

| Example | Latex Association | % Latex | Ratio | Oil | % Oil | % Surfactant |
|---|---|---|---|---|---|---|
| A | Luviflex Soft:Baycusan C1001 | 3 | 3:1 | Phenyl Trimethicone | 1 | 0.10% |
| B | Luviflex Soft:Baycusan C1001 | 3 | 3:1 | Olive | 1 | 0.10% |
| C | Luviflex Soft:Baycusan C1001 | 3 | 1:1 | Argan | 2 | 0.20% |
| D | Luviflex Soft:Baycusan C1001 | 3 | 1:1 | Jojoba | 2 | 0.20% |
| E | Luviflex Soft:Baycusan C1001 | 2 | 1:1 | Phenyl Trimethicone | 2 | 0.20% |
| F | Luviflex Soft:Baycusan C1001 | 3 | 3:1 | Phenyl Trimethicone | 12 | 1.20% |
| G | Luviflex Soft:Baycusan C1001 | 3 | 1:1 | Olive | 2 | 0.20% |
| H | Luviflex Soft:Baycusan C1001 | 3 | 3:1 | Olive | 2 | 0.20% |
| I | Luviflex Soft:Baycusan C1001 | 3 | 3:1 | Olive | 5 | 0.50% |
| J | Luviflex Soft:Baycusan C1001 | 3 | 3:1 | Olive | 10 | 1.00% |
| K | Luviflex Soft:Baycusan C1001 | 2 | 1:1 | Dimethicone | 2 | 0.20% |
| L | Luviflex Soft:Baycusan C1001 | 3 | 3:1 | Dimethicone | 5 | 0.50% |
| M | Luviflex Soft:Baycusan C1001 | 3 | 3:1 | Dimethicone | 10 | 1.00% |

TABLE 1-continued

| Example | Latex Association | % Latex | Ratio | Oil | % Oil | % Surfactant |
|---|---|---|---|---|---|---|
| N | Luviflex Soft:Baycusan C1001 | 2 | 3:1 | Tea tree Oil | 2 | 0.20% |
| O | Luviflex Soft:Daitosol SJ | 3 | 3:1 | Phenyl Trimethicone | 2 | 0.20% |
| P | Joncryl 77:Baycusan C1001 | 3 | 3:1 | Phenyl Trimethicone | 2 | 0.20% |
| Q | Joncryl 77:Baycusan C1001 | 3 | 3:1 | Phenyl Trimethicone | 5 | 0.50% |
| R | Joncryl 77:Baycusan C1001 | 3 | 2:1 | Phenyl Trimethicone | 2 | 0.20% |
| S | Joncryl 77:Baycusan C1001 | 3 | 1:1 | Phenyl Trimethicone | 2 | 0.20% |
| T | Syntran 5620:Baycusan C1001 | 3 | 3:1 | Phenyl Trimethicone | 2 | 0.20% |
| U | Syntran 5620:Baycusan C1001 | 3 | 2:1 | Phenyl Trimethicone | 2 | 0.20% |
| V | Syntran 5620:Baycusan C1001 | 3 | 1:1 | Phenyl Trimethicone | 2 | 0.20% |
| W | Joncryl 77:Daitosol SJ | 3 | 3:1 | Phenyl Trimethicone | 2 | 0.20% |
| X | Joncryl 77:Daitosol SJ | 3 | 3:1 | Phenyl Trimethicone | 5 | 0.50% |
| Y | Joncryl 77:Daitosol SJ | 3 | 2:1 | Phenyl Trimethicone | 2 | 0.20% |
| Z | Joncryl 77:Daitosol SJ | 3 | 1:1 | Phenyl Trimethicone | 2 | 0.20% |
| AA | Syntran 5620:Daitosol SJ | 3 | 3:1 | Phenyl Trimethicone | 2 | 0.20% |
| BB | Syntran 5620:Daitosol SJ | 3 | 2:1 | Phenyl Trimethicone | 2 | 0.20% |
| CC | Syntran 5620:Daitosol SJ | 3 | 1:1 | Phenyl Trimethicone | 2 | 0.20% |
| DD | Balance CR:Baycusan C1001 | 3 | 3:1 | Phenyl Trimethicone | 2 | 0.20% |
| EE | Balance CR:Baycusan C1001 | 3 | 2:1 | Phenyl Trimethicone | 2 | 0.20% |
| FF | Balance CR:Baycusan C1001 | 3 | 1:1 | Phenyl Trimethicone | 2 | 0.20% |
| GG | Dermacryl AQF:Baycusan C1001 | 3 | 3:1 | Phenyl Trimethicone | 2 | 0.20% |
| HH | Dermacryl AQF:Baycusan C1001 | 3 | 2:1 | Phenyl Trimethicone | 2 | 0.20% |
| II | Dermacryl AQF:Baycusan C1001 | 3 | 1:1 | Phenyl Trimethicone | 2 | 0.20% |
| JJ | Balance CR:Daitosol SJ | 3 | 3:1 | Phenyl Trimethicone | 2 | 0.20% |
| KK | Balance CR:Daitosol SJ | 3 | 2:1 | Phenyl Trimethicone | 2 | 0.20% |
| LL | Balance CR:Daitosol SJ | 3 | 1:1 | Phenyl Trimethicone | 2 | 0.20% |
| MM | Dermacryl AQF:Daitosol SJ | 3 | 3:1 | Phenyl Trimethicone | 2 | 0.20% |
| NN | Dermacryl AQF:Daitosol SJ | 3 | 2:1 | Phenyl Trimethicone | 2 | 0.20% |
| OO | Dermacryl AQF:Daitosol SJ | 3 | 1:1 | Phenyl Trimethicone | 2 | 0.20% |

All O/W emulsions A-OO were observed and were noted to be stable at room temperature and pressure for one month.

Example 2

Shine Measurement

The following sample products were applied to a swatch of wet, bleached hair (0.2 g product/g hair).

| Treatment | Shine (Reich-Robbins) |
|---|---|
| Latex (2% of Luviflex Soft/Baycusan C1001, 1:1) | 9.29 |
| Latex + 2% Jojoba Oil + 0.2% Surfactant 1 | 9.85 |
| Latex + 2% Dimethicone + 0.2% Surfactant 2 | 10.01 |
| Latex + 2% Olive Oil + 0.2% Surfactant 3 | 10.48 |
| Latex + 2% Phenyl Trimethicone + 0.2% Surfactant 4 | 11.56 |
| Commercial styling product containing 6% oil | 7.81 |

The surfactant mixtures used were as follows: Surfactant 1: Gyceryl Stearate & PEG-100 Stearate from Croda, 0.06% and Glyceryl Stearate from Ashland, 0.14%; Surfactant 2: Gyceryl Stearate & PEG-100 Stearate, 0.05% and Glyceryl Stearate, 0.15%; Surfactant 3: Gyceryl Stearate & PEG-100 Stearate, 0.12% and Glyceryl Stearate, 0.08%; and Surfactant 4: Gyceryl Stearate & PEG-100 Stearate, 0.12% and Glyceryl Stearate, 0.08%.

The treated hair was blow-dried with a comb then mounted on a photogoniometer to measure the shine. As seen above, it was observed that hair treated with the O/W emulsions provided more shine than the latex alone or a commercial product having 6% oil.

Example 3

Greasiness Measurement

Bleached hair was treated (0.5 g product/g hair) with a solution of 3% latex (Luviflex Soft/Baycusan c1001, 3:1 ratio)+12% Phenyl Trimethicone+1.2% surfactants (Gyceryl Stearate & PEG-100 Stearate, 0.72% and Glyceryl Stearate, 0.48%), and a commercial product containing 11% Oil. The treated hair was allowed to dry at room temperature overnight. The hair was placed between two blotting papers and put under a 3.5 kg weight for 30 seconds. The amount of oil soaked up by the blotting papers represents the change of the color spreading on the sheets. Also, an increase in the weight of the blotting paper reflects the amount of oil being absorbed. The results (n=3) are shown below.

| Treatment | Area of Soaked Oil | Weight (mg) |
|---|---|---|
| Latex emulsion containing 12% Oil | + | 0.7 +/− 0.33 |
| Commercial product containing 11% Oil | +++ | 14.73 +/− 1.9 |

It was observed that hair treated with the O/W emulsions was less greasy, as less oil was transferred.

Example 4

Foam Property of a Mousse

Two mousse formulations were prepared: (i) Mousse formulation 1: 2% Olive oil, 0.15% PEG 100-Glyceryl Stearate, 0.05% Glyceryl Stearate, 0.2% Hydroxypropyl Guar, 0.2% Ultrez-20; and (ii) Mousse formulation 2: 2% Olive oil, 0.15% PEG 100-Glyceryl Stearate, 0.05% Glyceryl Stearate, 0.2% Hydroxypropyl Guar, 0.2% Ultrez-20, 3% latex (Luviflex Soft/Baycusan C1001, 3:1). The foam properties of each formulation were observed, as follows.

| Product | Foam property |
|---|---|
| Mousse 1 | No foam |
| Mousse 2 | Foam stable for at least 30 seconds |

Thus, the addition of the latex particles to Mousse formulation 2 dramatically increased the stability thereof, relative to Mousse formulation 1 having no latex.

Example 5

In-Vivo Testing

The following hair creams were tested: (i) Hair Cream 1 containing 3% Latex ((Luviflex Soft/Baycusan C1001, 3:1), 5% Phenyl Trimethicone, and 0.5% surfactants (Gyceryl Stearate & PEG-100 Stearate, 0.3% and Glyceryl Stearate, 0.2%); and (ii) Hair Cream 2, a commercial product, containing 5% Olive Oil+1% Coconut Oil.

Hair treated with Hair Cream 1 showed more shine, less oiliness, cleaner feel, more suppleness, and more hair discipline. A recheck after 4 hours also showed hair treated with Hair Cream 1 had more style control, more curl definition, and more frizz control.

These results demonstrate that hair treated with a composition according to the disclosure has greater desired properties than the commercial product.

Example 6

Comparative

As a comparison, the following dispersions were made by:
(i) heating the oil (and surfactants where present: Gyceryl Stearate & PEG-100 Stearate, 0.3% and Glyceryl Stearate, 0.2%) at 80° C. until homogeneous;
(ii) adding the oil/surfactants solution to water at 60° C. while homogenizing at 6000 rpm until the solution cools to room temperature; (iii) adding latex (where present) and stirring for 10 minutes. The stability of the resulting solutions is shown below.

| Dispersion | Stability |
| --- | --- |
| 5% Olive Oil | Separation |
| 5% Olive Oil + 0.5% Surfactants | Separation |
| 5% Olive Oil + 3% Latex | Separation |
| 3% Latex + 5% Olive Oil + 0.5% Surfactants | Stable for at least 1 month |

It can be seen that the emulsions according to the disclosure are more stable than the other preparations.

What is claimed is:

1. A hair styling composition comprising an oil-in-water emulsion, the oil-in-water emulsion comprising:
   (a) an aqueous dispersion of particles of a mixture of an acrylate latex and a polyurethane latex,
   (b) an oil phase, and
   (c) at least one surfactant,
   wherein the amount of the (a) aqueous dispersion of particles in combination with the (c) at least one surfactant is sufficient to stabilize the oil-in-water emulsion;
   wherein the total amount of surfactant present in the oil-in-water emulsion is not, by itself, sufficient to stabilize the emulsion; and
   wherein the emulsion is stable.

2. The hair styling composition of claim 1, wherein the oil phase comprises at least one water-insoluble component chosen from volatile oils, non-volatile oils, UV agents, and antioxidants.

3. The hair styling composition of claim 1, wherein the at least one surfactant has an HLB value approximately the same as the HLB value of the water-insoluble component.

4. The hair styling composition of claim 2, wherein the at least one water-insoluble component is present in the oil-in-water emulsion in an amount ranging from about 0.1% to about 50% by weight, relative to the total weight of the emulsion.

5. The hair styling composition of claim 3, wherein the at least one surfactant is chosen from non-ionic and anionic surfactants.

6. The hair styling composition of claim 1, wherein the aqueous dispersion of particles is present in the oil-in-water emulsion in an amount ranging from about 0.5% to about 10% by weight as polymeric active material (dry weight basis), relative to the total weight of the emulsion.

7. The hair styling composition of claim 1, further comprising at least one additional component chosen from solvents, wax dispersions, oils, rheology modifiers, thickening agents, structuring agents, vitamins, plant extracts, or propellants.

8. The hair styling composition of claim 7, comprising at least one solvent.

9. The hair styling composition of claim 8, comprising at least one wax dispersion, wherein said wax dispersion comprises particles of natural and/or synthetic waxes dispersed in a surfactant mixture comprising nonionic and/or ionic surfactants.

10. A method of making an oil-in-water emulsion, said oil-in-water emulsion comprising:
    (a) an aqueous dispersion of particles of a mixture of an acrylate latex and a polyurethane latex,
    (b) an oil phase, and
    (c) at least one surfactant,
    wherein the amount of the (a) aqueous dispersion of particles in combination with the (c) at least one surfactant is sufficient to stabilize the oil-in-water emulsion; and
    wherein the (c) at least one surfactant is present in the oil-in-water emulsion in an amount that is not, by itself, sufficient to stabilize the emulsion,
    wherein the method comprises:
    combining (a) the aqueous dispersion of particles, (b) the oil phase, and (c) the at least one surfactant,
    optionally mixing the combined components, and
    homogenizing the combined components under either low-pressure or high-pressure homogenization.

11. The method of claim 10, wherein the oil-in-water emulsion is stable.

12. The method of claim 10, comprising mixing (a) the aqueous dispersion, (b) the at least one oil phase, and (c) the at least one surfactant, prior to said homogenization.

13. The method of claim 8, wherein the homogenization process is repeated from 2 to 10 times.

14. A method of styling the hair, said method comprising applying an oil-in-water emulsion to the hair, said oil-in-water emulsion comprising:
    (a) an aqueous dispersion of particles of a mixture of an acrylate latex and a polyurethane latex,
    (b) an oil phase, and
    (c) at least one surfactant,
    wherein the amount of the (a) aqueous dispersion of particles in combination with the (c) at least one surfactant is sufficient to stabilize the oil-in-water emulsion; and wherein the (c) at least one surfactant is present in the oil-in-water emulsion in an amount that is not, by itself, sufficient to stabilize the emulsion.

15. A method of styling the hair, said method comprising applying to the hair a composition comprising:
  (1) an oil-in-water emulsion comprising:
    (a) an aqueous dispersion of particles of a mixture of an acrylate latex and a polyurethane latex,
    (b) an oil phase, and
    (c) at least one surfactant,
  wherein the amount of the (a) aqueous dispersion of particles in combination with the (c) at least one surfactant is sufficient to stabilize the oil-in-water emulsion; and
  wherein the (c) at least one surfactant is present in the oil-in-water emulsion in an amount that is not, by itself, sufficient to stabilize the emulsion; and
  (2) at least one additional component chosen from solvents, wax dispersions, oils, rheology modifiers, thickening agents, structuring agents, propellants, vitamins, or plant extracts.

16. The method of claim 15, wherein the composition comprises at least one solvent.

17. The method of claim 16, wherein the composition further comprises at least one wax dispersion, wherein said wax dispersion comprises particles of natural and/or synthetic waxes dispersed in a surfactant mixture comprising nonionic and/or ionic surfactants.

* * * * *